(12) United States Patent
Toyazaki et al.

(10) Patent No.: US 9,487,806 B2
(45) Date of Patent: Nov. 8, 2016

(54) METHOD FOR PRODUCING L-AMINO ACID

(71) Applicant: AJINOMOTO CO., INC., Tokyo (JP)

(72) Inventors: Miku Toyazaki, Kanagawa (JP); Keiko Noguchi, Kanagawa (JP); Mika Moriya, Kanagawa (JP); Yuri Uehara, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 14/735,303

(22) Filed: Jun. 10, 2015

(65) Prior Publication Data

US 2015/0275246 A1 Oct. 1, 2015

Related U.S. Application Data

(63) Continuation of application No. PCT/JP2014/077993, filed on Oct. 21, 2014.

(30) Foreign Application Priority Data

Oct. 21, 2013 (JP) ................. 2013-218221

(51) Int. Cl.
*C12P 13/04* (2006.01)
*C12P 13/08* (2006.01)
*C12N 15/70* (2006.01)

(52) U.S. Cl.
CPC ............... *C12P 13/08* (2013.01); *C12P 13/04* (2013.01); *C12N 15/70* (2013.01)

(58) Field of Classification Search
None
See application file for complete search history.

(56) References Cited

U.S. PATENT DOCUMENTS

| | | |
|---|---|---|
| 5,168,056 A | 12/1992 | Frost |
| 5,776,736 A | 7/1998 | Frost et al. |
| 5,906,925 A | 5/1999 | Liao |
| 8,030,036 B2 | 10/2011 | Van Dien et al. |
| 8,722,370 B2 | 5/2014 | Filippov et al. |
| 2009/0286290 A1 | 11/2009 | Hara et al. |
| 2010/0209977 A1 | 8/2010 | Takumi et al. |

FOREIGN PATENT DOCUMENTS

| | | |
|---|---|---|
| WO | WO2004/108840 | 12/2004 |
| WO | WO2007/136762 | 11/2007 |
| WO | WO2010/042664 | 4/2010 |
| WO | WO2011/152565 | 12/2011 |

OTHER PUBLICATIONS

Mitev et al., "Inhibition of Intracellular Growth of *Salmonella enterica* Serovar Typhimurium in Tissue Culture by Antisense Peptide Phosphorodiamidate Morpholino Oligomer", Antimicrob. Agents Chemother. 53:3700-3704, 2009.*
De Lay et al., "Gene-Specific Random Mutagenesis of *Escherichia coli* In Vivo: Isolation of Temperature-Sensitive Mutations in the Acyl Carrier Protein of Fatty Acid Synthesis", J. Bacteriol. 188:287-296, 2006.*
De Lay, N. R., et al., "In Vivo Functional Analyses of the Type II Acyl Carrier Proteins of Fatty Acid Biosynthesis," J. Biol. Chem. 2007;282(28):20319-20328.
Zhang, Y., et al., "Polar Allele Duplication for Transcriptional Analysis of Consecutive Essential Genes: Application to a Cluster of *Escherichia coli* Fatty Acid Biosynthetic Genes," J. Bacteriol. 1996;178(12):3614-3620.
International Search Report for PCT Patent App. No. PCT/JP2014/077993 (Jan. 27, 2015).
English translation of the Written Opinion for PCT Patent App. No. PCT/JP2014/077993 (Jan. 27, 2015).
Chan, D. I., et al., "Review Article: Current understanding of fatty acid biosynthesis and the acyl carrier protein," Biochem. J. 2010;430:1-19.
Rawlings, M., et al., "The Gene Encoding *Escherichia coli* Acyl Carrier Protein Lies within a Cluster of Fatty Acid Biosynthetic Genes," J. Biol. Chem. 1992;267(9):5751-5754.
Supplementary European Search Report for European Patent App. No. 14835548.0 (Apr. 25, 2016).

* cited by examiner

*Primary Examiner* — David J Steadman
(74) *Attorney, Agent, or Firm* — SHelly Guest Cermak; Cermak Nakajima & McGowan LLP

(57) ABSTRACT

A method for producing of an L-amino acid is provided. An L-amino acid is produced by culturing a bacterium belonging to the family Enterobacteriaceae and having an L-amino acid-producing ability, which has been modified so that the acpP-fabF operon is attenuated, in a medium, and collecting the L-amino acid from the medium or cells of the bacterium.

9 Claims, No Drawings

SEQUENCE LISTING

```
<160> NUMBER OF SEQ ID NOS: 16

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
tttttttctg cgcgacgggt gaaactttgc atgtg                             35

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
aaaagcaggc ttcaaaaagc taagaaaaaa ggcccg                            36
```

-continued

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tacgaaaacc atagcgaaag cgagt                                          25

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
actcgctttc gctatggttt tcgta                                          25

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cgggtgaaac tttgcatgtg                                                20

<210> SEQ ID NO 6
<211> LENGTH: 68
<212> TYPE: DNA
<213> ORGANISM: Artificial Sequence
<220> FEATURE:
<223> OTHER INFORMATION: primer

<400> SEQUENCE: 6
cagagaattg ttagtgtggc agcatgttca ctacggaaca agtcggaata cgctcaagtt    60
agtataaa                                                             68

<210> SEQ ID NO 7
<211> LENGTH: 1776
<212> TYPE: DNA
<213> ORGANISM: Escherichia coli MG1655
<220> FEATURE:
<221> NAME/KEY: CDS
<222> LOCATION: (211)..(447)
<220> FEATURE:
<221> NAME/KEY: CDS
<222> LOCATION: (535)..(1776)

<400> SEQUENCE: 7
ccgcgatttg cacaaaatgc tcatgttgcg cgcagtctgc gtggttatga gtaataatta    60
gtgcaaaatg atttgcgtta ttgggggta aggcctcaaa ataacgtaaa atcgtggtaa   120
gacctgccgg gatttagttg caaatttttc aacattttat acactacgaa accatcgcg   180 aaagcgagtt ttgataggaa atttaagagt atg agc act atc gaa gaa cgc gtt   234
                                 Met Ser Thr Ile Glu Glu Arg Val
                                  1               5 aag aaa att atc ggc gaa cag ctg ggc gtt aag cag gaa gaa gtt acc   282
Lys Lys Ile Ile Gly Glu Gln Leu Gly Val Lys Gln Glu Glu Val Thr
         10              15                  20

-continued

| | | |
|---|---|---|
| aac aat gct tct ttc gtt gaa gac ctg ggc gcg gat tct ctt gac acc<br>Asn Asn Ala Ser Phe Val Glu Asp Leu Gly Ala Asp Ser Leu Asp Thr<br>25                             30                         35                       40 | | 330 |
| gtt gag ctg gta atg gct ctg gaa gaa gag ttt gat act gag att ccg<br>Val Glu Leu Val Met Ala Leu Glu Glu Glu Phe Asp Thr Glu Ile Pro<br>                      45                       50                       55 | | 378 |
| gac gaa gaa gct gag aaa atc acc acc gtt cag gct gcc att gat tac<br>Asp Glu Glu Ala Glu Lys Ile Thr Thr Val Gln Ala Ala Ile Asp Tyr<br>                 60                       65                     70 | | 426 |
| atc aac ggc cac cag gcg taa gtgaacatct ccaggcggtc gttcgaccgc<br>Ile Asn Gly His Gln Ala<br>               75 | | 477 |
| ctgagtttta tcttttgtc ccactagaat catttttcc ctccctggag gacaaac | | 534 |
| gtg tct aag cgt cgt gta gtt gtg acc gga ctg ggc atg ttg tct cct<br>Met Ser Lys Arg Arg Val Val Val Thr Gly Leu Gly Met Leu Ser Pro<br>               80                       85                       90 | | 582 |
| gtc ggc aat acc gta gag tct acc tgg aaa gct ctg ctt gcc ggt cag<br>Val Gly Asn Thr Val Glu Ser Thr Trp Lys Ala Leu Leu Ala Gly Gln<br>95                           100                      105                    110 | | 630 |
| agt ggc atc agc cta atc gac cat ttc gat act agc gcc tat gca acg<br>Ser Gly Ile Ser Leu Ile Asp His Phe Asp Thr Ser Ala Tyr Ala Thr<br>                     115                      120                    125 | | 678 |
| aaa ttt gct ggc tta gta aag gat ttt aac tgt gag gac att atc tcg<br>Lys Phe Ala Gly Leu Val Lys Asp Phe Asn Cys Glu Asp Ile Ile Ser<br>            130                      135                    140 | | 726 |
| cgc aaa gaa cag cgc aag atg gat gcc ttc att caa tat gga att gtc<br>Arg Lys Glu Gln Arg Lys Met Asp Ala Phe Ile Gln Tyr Gly Ile Val<br>                 145                      150                    155 | | 774 |
| gct ggc gtt cag gcc atg cag gat tct ggc ctt gaa ata acg gaa gag<br>Ala Gly Val Gln Ala Met Gln Asp Ser Gly Leu Glu Ile Thr Glu Glu<br>            160                      165                    170 | | 822 |
| aac gca acc cgc att ggt gcc gca att ggc tcc ggg att ggc ggc ctc<br>Asn Ala Thr Arg Ile Gly Ala Ala Ile Gly Ser Gly Ile Gly Gly Leu<br>175                       180                      185                    190 | | 870 |
| gga ctg atc gaa gaa aac cac aca tct ctg atg aac ggt ggt cca cgt<br>Gly Leu Ile Glu Glu Asn His Thr Ser Leu Met Asn Gly Gly Pro Arg<br>                 195                      200                    205 | | 918 |
| aag atc agc cca ttc ttc gtt ccg tca acg att gtg aac atg gtg gca<br>Lys Ile Ser Pro Phe Phe Val Pro Ser Thr Ile Val Asn Met Val Ala<br>            210                      215                    220 | | 966 |
| ggt cat ctg act atc atg tat ggc ctg cgt ggc ccg agc atc tct atc<br>Gly His Leu Thr Ile Met Tyr Gly Leu Arg Gly Pro Ser Ile Ser Ile<br>               225                      230                    235 | | 1014 |
| gcg act gcc tgt act tcc ggc gtg cac aac att ggc cat gct gcg cgt<br>Ala Thr Ala Cys Thr Ser Gly Val His Asn Ile Gly His Ala Ala Arg<br>            240                      245                    250 | | 1062 |
| att atc gcg tat ggc gat gct gac gtg atg gtt gca ggt ggc gca gag<br>Ile Ile Ala Tyr Gly Asp Ala Asp Val Met Val Ala Gly Gly Ala Glu<br>255                       260                      265                    270 | | 1110 |
| aaa gcc agt acg ccg ctg ggc gtt ggt ggt ttt ggc gcg gca cgt gca<br>Lys Ala Ser Thr Pro Leu Gly Val Gly Gly Phe Gly Ala Ala Arg Ala<br>                     275                      280                    285 | | 1158 |
| tta tct acc cgc aat gat aac ccg caa gcg gcg agc cgc ccg tgg gat<br>Leu Ser Thr Arg Asn Asp Asn Pro Gln Ala Ala Ser Arg Pro Trp Asp<br>            290                      295                    300 | | 1206 |
| aaa gag cgt gat ggt ttc gta ctg ggc gat ggt gcc ggt atg ctg gta<br>Lys Glu Arg Asp Gly Phe Val Leu Gly Asp Gly Ala Gly Met Leu Val<br>                 305                      310                    315 | | 1254 |

```
ctt gaa gag tac gaa cac gcg aaa aaa cgt ggt gcg aaa att tac gct         1302
Leu Glu Glu Tyr Glu His Ala Lys Lys Arg Gly Ala Lys Ile Tyr Ala
    320                 325                 330 gaa ctc gtc ggc ttt ggt atg agc agc gat gct tat cat atg acg tca         1350
Glu Leu Val Gly Phe Gly Met Ser Ser Asp Ala Tyr His Met Thr Ser
335                 340                 345                 350 ccg cca gaa aat ggc gca ggc gca gct ctg gcg atg gca aat gct ctg         1398
Pro Pro Glu Asn Gly Ala Gly Ala Ala Leu Ala Met Ala Asn Ala Leu
                355                 360                 365 cgt gat gca ggc att gaa gcg agt cag att ggc tac gtt aac gcg cac         1446
Arg Asp Ala Gly Ile Glu Ala Ser Gln Ile Gly Tyr Val Asn Ala His
            370                 375                 380 ggt act tct acg ccg gct ggc gat aaa gct gaa gcg cag gcg gtg aaa         1494
Gly Thr Ser Thr Pro Ala Gly Asp Lys Ala Glu Ala Gln Ala Val Lys
        385                 390                 395 acc atc ttc ggt gaa gct gca agc cgt gtg ttg gta agc tcc acg aaa         1542
Thr Ile Phe Gly Glu Ala Ala Ser Arg Val Leu Val Ser Ser Thr Lys
    400                 405                 410 tct atg acc ggt cac ctg tta ggt gcg gcg ggt gca gta gaa tct atc         1590
Ser Met Thr Gly His Leu Leu Gly Ala Ala Gly Ala Val Glu Ser Ile
415                 420                 425                 430 tac tcc atc ctg gcg ctg cgc gat cag gct gtt ccg cca acc atc aac         1638
Tyr Ser Ile Leu Ala Leu Arg Asp Gln Ala Val Pro Pro Thr Ile Asn
                435                 440                 445 ctg gat aac ccg gat gaa ggt tgc gat ctg gat ttc gta ccg cac gaa         1686
Leu Asp Asn Pro Asp Glu Gly Cys Asp Leu Asp Phe Val Pro His Glu
            450                 455                 460 gcg cgt cag gtt agc gga atg gaa tac act ctg tgt aac tcc ttc ggc         1734
Ala Arg Gln Val Ser Gly Met Glu Tyr Thr Leu Cys Asn Ser Phe Gly
        465                 470                 475 ttc ggt ggc act aat ggt tct ttg atc ttt aaa aag atc taa             1776
Phe Gly Gly Thr Asn Gly Ser Leu Ile Phe Lys Lys Ile
    480                 485                 490

<210> SEQ ID NO 8
<211> LENGTH: 78
<212> TYPE: PRT
<213> ORGANISM: Escherichia coli MG1655

<400> SEQUENCE: 8

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
                20                  25                  30

Leu Gly Ala Asp Ser Leu Asp Thr Val Glu Leu Val Met Ala Leu Glu
            35                  40                  45

Glu Glu Phe Asp Thr Glu Ile Pro Asp Glu Glu Ala Glu Lys Ile Thr
        50                  55                  60

Thr Val Gln Ala Ala Ile Asp Tyr Ile Asn Gly His Gln Ala
65                  70                  75

<210> SEQ ID NO 9
<211> LENGTH: 413
<212> TYPE: PRT
<213> ORGANISM: Escherichia coli MG1655
```

<400> SEQUENCE: 9

Met Ser Lys Arg Arg Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
            35                  40                  45

Lys Phe Ala Gly Leu Val Lys Asp Phe Asn Cys Glu Asp Ile Ile Ser
50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
            115                 120                 125

Lys Ile Ser Pro Phe Phe Val Pro Ser Thr Ile Val Asn Met Val Ala
130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
            195                 200                 205

Leu Ser Thr Arg Asn Asp Asn Pro Gln Ala Ala Ser Arg Pro Trp Asp
210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
            260                 265                 270

Pro Pro Glu Asn Gly Ala Gly Ala Ala Leu Ala Met Ala Asn Ala Leu
            275                 280                 285

Arg Asp Ala Gly Ile Glu Ala Ser Gln Ile Gly Tyr Val Asn Ala His
290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
            355                 360                 365

Leu Asp Asn Pro Asp Glu Gly Cys Asp Leu Asp Phe Val Pro His Glu
370                 375                 380

Ala Arg Gln Val Ser Gly Met Glu Tyr Thr Leu Cys Asn Ser Phe Gly
385                 390                 395                 400

Phe Gly Gly Thr Asn Gly Ser Leu Ile Phe Lys Lys Ile
                405                 410

```
<210> SEQ ID NO 10
<211> LENGTH: 1912
<212> TYPE: DNA
<213> ORGANISM: Pantoea ananatis AJ13355
<220> FEATURE:
<221> NAME/KEY: CDS
<222> LOCATION: (211)..(585)
<220> FEATURE:
<221> NAME/KEY: CDS
<222> LOCATION: (707)..(1912)

<400> SEQUENCE: 10
ccgggcttca tagagactga catgacgcgg gcactgaacg aagatcaacg ttccggtatt      60
ctggcggagg tcccagcggg tcgtttaggc gaagcgcagg aaattgctaa tgccgttgca     120
ttcttagcct ctgacgaagc agcctacatc acgggtgaga cgctgcacgt caatggcggc     180
atgtatatgg tctgataatc acgaaatcat ttg cat tat ttg cgg ata aaa ccg     234
                                  Met His Tyr Leu Arg Ile Lys Pro
                                    1               5 cac aat agc gta aaa tcg tgg ttc gac cag ccg gga ttt tgt tgc atc     282
His Asn Ser Val Lys Ser Trp Phe Asp Gln Pro Gly Phe Cys Cys Ile
         10                  15                  20 ttt ttc aac att tta tac act acg aaa acc atc gcg aaa gcg agt ttt     330
Phe Phe Asn Ile Leu Tyr Thr Thr Lys Thr Ile Ala Lys Ala Ser Phe
 25                  30                  35                  40 gat agg aaa tta aat agt atg agc gat atc gaa caa cgc gtt aag aaa     378
Asp Arg Lys Leu Asn Ser Met Ser Asp Ile Glu Gln Arg Val Lys Lys
                 45                  50                  55 atc atc agt gag cag ctg ggt gtg aaa gag gaa gaa gtg acc aac tct     426
Ile Ile Ser Glu Gln Leu Gly Val Lys Glu Glu Glu Val Thr Asn Ser
             60                  65                  70 gca tct ttc gta gaa gac ctg ggt gcc gat tct ctt gat acc gtt gag     474
Ala Ser Phe Val Glu Asp Leu Gly Ala Asp Ser Leu Asp Thr Val Glu
         75                  80                  85 ctg gta atg gct ctg gaa gaa gag ttt gat act gaa att cca gac gaa     522
Leu Val Met Ala Leu Glu Glu Glu Phe Asp Thr Glu Ile Pro Asp Glu
     90                  95                 100 gaa gct gag aaa atc act acc gtt cag gca gcg atc gac tat atc aat     570
Glu Ala Glu Lys Ile Thr Thr Val Gln Ala Ala Ile Asp Tyr Ile Asn
105                 110                 115                 120 agc cat aaa ggc taa tgaatatctt caggcggtca tatgaccgcc tgagttttat    625
Ser His Lys Gly gtttgcccca caatagtcat ttttatccct ccctggagga cgaacgtgtc taagcgtcgt     685
gtagttgtga ctggtcttgg c atg ttg tct cct gtc ggc aat acc gta gag       736
                        Met Leu Ser Pro Val Gly Asn Thr Val Glu
                            125                 130 tct acc tgg agt gct ctc ctt gcc ggt cag agc ggc att aac ctg atc     784
Ser Thr Trp Ser Ala Leu Leu Ala Gly Gln Ser Gly Ile Asn Leu Ile
135                 140                 145                 150 gac cat ttt gat acc agc gcc tat gca aca cgt ttt gca ggc ctg gta     832
Asp His Phe Asp Thr Ser Ala Tyr Ala Thr Arg Phe Ala Gly Leu Val
                155                 160                 165 aga gat ttt aat tgc gat gac ttt atc tct cgt aaa gat caa cgc aag     880
Arg Asp Phe Asn Cys Asp Asp Phe Ile Ser Arg Lys Asp Gln Arg Lys
            170                 175                 180 atg gat gac ttc att cag tac ggc atc gtg gca ggc att cag gcc atg     928
Met Asp Asp Phe Ile Gln Tyr Gly Ile Val Ala Gly Ile Gln Ala Met
        185                 190                 195 cag gac agc ggt ctg gtt gtg acc gac gaa aat gca ggc cgg gtt ggc     976
Gln Asp Ser Gly Leu Val Val Thr Asp Glu Asn Ala Gly Arg Val Gly
    200                 205                 210
```

```
gca gca att ggt tcg ggc atc ggg ggc ttg ggt ctt att gaa gac aac      1024
Ala Ala Ile Gly Ser Gly Ile Gly Gly Leu Gly Leu Ile Glu Asp Asn
215                 220                 225                 230 cat acc tct ctg gtg aac ggt ggc ccg cgt aaa att agc cca ttc ttt      1072
His Thr Ser Leu Val Asn Gly Gly Pro Arg Lys Ile Ser Pro Phe Phe
                235                 240                 245 gtg cct tcc aca atc gtc aat atg gtg gcg ggg cat ctc acc atc atg      1120
Val Pro Ser Thr Ile Val Asn Met Val Ala Gly His Leu Thr Ile Met
            250                 255                 260 tat ggc ctg aaa ggc ccc agc atc tcc att gcg acc gcc tgt acg tct      1168
Tyr Gly Leu Lys Gly Pro Ser Ile Ser Ile Ala Thr Ala Cys Thr Ser
        265                 270                 275 ggc gtg cac aat atc ggt cat gct gca cgt atc atc gcc tat aac gat      1216
Gly Val His Asn Ile Gly His Ala Ala Arg Ile Ile Ala Tyr Asn Asp
    280                 285                 290 gcc gac gtg atg ctg gcg ggc ggt gcg gaa aaa gcc agt acg cca ctt      1264
Ala Asp Val Met Leu Ala Gly Gly Ala Glu Lys Ala Ser Thr Pro Leu
295                 300                 305                 310 ggc gtt ggc gga ttc ggc gcg gca cgt gcg ctg tcg acg cgt aac gaa      1312
Gly Val Gly Gly Phe Gly Ala Ala Arg Ala Leu Ser Thr Arg Asn Glu
                315                 320                 325 aat ccc cag gcg gca agc cgt cca tgg gat aaa gac cgt gat gga ttt      1360
Asn Pro Gln Ala Ala Ser Arg Pro Trp Asp Lys Asp Arg Asp Gly Phe
                330                 335                 340 gta ctg ggc gac ggc gct ggc att atc gta ctg gaa gag tat gag cat      1408
Val Leu Gly Asp Gly Ala Gly Ile Ile Val Leu Glu Glu Tyr Glu His
            345                 350                 355 gct aag aaa cgt ggc gca aaa atc tat gcg gaa att gtg ggc ttt ggg      1456
Ala Lys Lys Arg Gly Ala Lys Ile Tyr Ala Glu Ile Val Gly Phe Gly
        360                 365                 370 atg agc agc gat gct tat cac atg acc tca ccg ccg gaa gac ggt tca      1504
Met Ser Ser Asp Ala Tyr His Met Thr Ser Pro Pro Glu Asp Gly Ser
375                 380                 385                 390 ggt gca gcc gct gcg atg atc aac gcg ctg cgt gat gcg cag atg acg      1552
Gly Ala Ala Ala Ala Met Ile Asn Ala Leu Arg Asp Ala Gln Met Thr
                395                 400                 405 cca gat aag att ggt tac gtc aat gca cac ggt acc tca acc cca gcc      1600
Pro Asp Lys Ile Gly Tyr Val Asn Ala His Gly Thr Ser Thr Pro Ala
                410                 415                 420 ggc gat aaa gcg gaa gcc cag gcg gtg aaa tcc gtt ttt ggt gca gca      1648
Gly Asp Lys Ala Glu Ala Gln Ala Val Lys Ser Val Phe Gly Ala Ala
            425                 430                 435 gcc agt acg gta atg gtc agc tcc acc aaa tcc atg acc ggc cat ctg      1696
Ala Ser Thr Val Met Val Ser Ser Thr Lys Ser Met Thr Gly His Leu
        440                 445                 450 ttg ggt gcg gcg ggc gcg gtt gag tcg atc tat tcg att ctg gcc ctg      1744
Leu Gly Ala Ala Gly Ala Val Glu Ser Ile Tyr Ser Ile Leu Ala Leu
455                 460                 465                 470 cgc gac cag gcg att cca ccg acg ctg aac ctg gat aat cct gat gaa      1792
Arg Asp Gln Ala Ile Pro Pro Thr Leu Asn Leu Asp Asn Pro Asp Glu
                475                 480                 485 ggt tgc gat ctt gat ttc gtt ccg cac acc gct cgt cag gtt tcg ggg      1840
Gly Cys Asp Leu Asp Phe Val Pro His Thr Ala Arg Gln Val Ser Gly
            490                 495                 500 ctg gaa tac acg ctg tgt aac tcc ttc ggc ttc ggt ggt acc aac ggc      1888
Leu Glu Tyr Thr Leu Cys Asn Ser Phe Gly Phe Gly Gly Thr Asn Gly
        505                 510                 515 tcg ctg att ttc cgt aaa atc taa                                      1912
Ser Leu Ile Phe Arg Lys Ile
        520                 525
```

```
<210> SEQ ID NO 11
<211> LENGTH: 124
<212> TYPE: PRT
<213> ORGANISM: Pantoea ananatis AJ13355

<400> SEQUENCE: 11

Met His Tyr Leu Arg Ile Lys Pro His Asn Ser Val Lys Ser Trp Phe
1               5                   10                  15

Asp Gln Pro Gly Phe Cys Cys Ile Phe Phe Asn Ile Leu Tyr Thr Thr
            20                  25                  30

Lys Thr Ile Ala Lys Ala Ser Phe Asp Arg Lys Leu Asn Ser Met Ser
        35                  40                  45

Asp Ile Glu Gln Arg Val Lys Lys Ile Ile Ser Glu Gln Leu Gly Val
    50                  55                  60

Lys Glu Glu Glu Val Thr Asn Ser Ala Ser Phe Val Glu Asp Leu Gly
65                  70                  75                  80

Ala Asp Ser Leu Asp Thr Val Glu Leu Val Met Ala Leu Glu Glu Glu
                85                  90                  95

Phe Asp Thr Glu Ile Pro Asp Glu Glu Ala Glu Lys Ile Thr Thr Val
            100                 105                 110

Gln Ala Ala Ile Asp Tyr Ile Asn Ser His Lys Gly
        115                 120

<210> SEQ ID NO 12
<211> LENGTH: 401
<212> TYPE: PRT
<213> ORGANISM: Pantoea ananatis AJ13355

<400> SEQUENCE: 12

Met Leu Ser Pro Val Gly Asn Thr Val Glu Ser Thr Trp Ser Ala Leu
1               5                   10                  15

Leu Ala Gly Gln Ser Gly Ile Asn Leu Ile Asp His Phe Asp Thr Ser
            20                  25                  30

Ala Tyr Ala Thr Arg Phe Ala Gly Leu Val Arg Asp Phe Asn Cys Asp
        35                  40                  45

Asp Phe Ile Ser Arg Lys Asp Gln Arg Lys Met Asp Asp Phe Ile Gln
    50                  55                  60

Tyr Gly Ile Val Ala Gly Ile Gln Ala Met Gln Asp Ser Gly Leu Val
65                  70                  75                  80

Val Thr Asp Glu Asn Ala Gly Arg Val Gly Ala Ala Ile Gly Ser Gly
                85                  90                  95

Ile Gly Gly Leu Gly Leu Ile Glu Asp Asn His Thr Ser Leu Val Asn
            100                 105                 110

Gly Gly Pro Arg Lys Ile Ser Pro Phe Phe Val Pro Ser Thr Ile Val
        115                 120                 125

Asn Met Val Ala Gly His Leu Thr Ile Met Tyr Gly Leu Lys Gly Pro
    130                 135                 140

Ser Ile Ser Ile Ala Thr Ala Cys Thr Ser Gly Val His Asn Ile Gly
145                 150                 155                 160

His Ala Ala Arg Ile Ile Ala Tyr Asn Asp Ala Asp Val Met Leu Ala
                165                 170                 175

Gly Gly Ala Glu Lys Ala Ser Thr Pro Leu Gly Val Gly Gly Phe Gly
            180                 185                 190

Ala Ala Arg Ala Leu Ser Thr Arg Asn Glu Asn Pro Gln Ala Ala Ser
        195                 200                 205
```

```
Arg Pro Trp Asp Lys Asp Arg Asp Gly Phe Val Leu Gly Asp Gly Ala
210                 215                 220
Gly Ile Ile Val Leu Glu Glu Tyr Glu His Ala Lys Lys Arg Gly Ala
225                 230                 235                 240
Lys Ile Tyr Ala Glu Ile Val Gly Phe Gly Met Ser Ser Asp Ala Tyr
                245                 250                 255
His Met Thr Ser Pro Pro Glu Asp Gly Ser Gly Ala Ala Ala Ala Met
            260                 265                 270
Ile Asn Ala Leu Arg Asp Ala Gln Met Thr Pro Asp Lys Ile Gly Tyr
        275                 280                 285
Val Asn Ala His Gly Thr Ser Thr Pro Ala Gly Asp Lys Ala Glu Ala
    290                 295                 300
Gln Ala Val Lys Ser Val Phe Gly Ala Ala Ser Thr Val Met Val
305                 310                 315                 320
Ser Ser Thr Lys Ser Met Thr Gly His Leu Leu Gly Ala Ala Gly Ala
                325                 330                 335
Val Glu Ser Ile Tyr Ser Ile Leu Ala Leu Arg Asp Gln Ala Ile Pro
            340                 345                 350
Pro Thr Leu Asn Leu Asp Asn Pro Asp Glu Gly Cys Asp Leu Asp Phe
        355                 360                 365
Val Pro His Thr Ala Arg Gln Val Ser Gly Leu Glu Tyr Thr Leu Cys
    370                 375                 380
Asn Ser Phe Gly Phe Gly Gly Thr Asn Gly Ser Leu Ile Phe Arg Lys
385                 390                 395                 400
Ile

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
aacagctggg cgttaagca                                                  19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gcccaggtct tcaacgaaag                                                 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cctgggaact gcatctgata                                                 20

<210> SEQ ID NO 16
<211> LENGTH: 20
<212> TYPE: DNA
<213> ORGANISM: Artificial Sequence
```

```
<220> FEATURE:
<223> OTHER INFORMATION: primer

<400> SEQUENCE: 16
tctacgcatt tcaccgctac                                              20
```

METHOD FOR PRODUCING L-AMINO ACID

This application is a Continuation of, and claims priority under 35 U.S.C. §120 to, International Application No. PCT/JP2014/077993, filed on Oct. 21, 2014, and claims priority therethrough under 35 U.S.C. §119 to Japanese Patent Application No. 2013-218221, filed Oct. 21, 2013, the entireties of which are incorporated by reference herein. Also, the Sequence Listing filed electronically herewith is hereby incorporated by reference (File name: 2015-06-10T_US-525_Seq_List; File size: 27 KB; Date recorded: Jun. 10, 2015).

BACKGROUND OF THE INVENTION

1. Field of the Invention

The present invention relates to a method for producing an L-amino acid using a bacterium. L-Amino acids are industrially useful as additives for animal feeds, ingredients in seasonings, foods and drinks, amino acid infusions, and so forth.

2. Brief Description of the Related Art

L-Amino acids are industrially produced by, for example, fermentation using various microorganisms having an L-amino acid-producing ability. Examples of methods for producing an L-amino acid by fermentation include, for example, methods using a wild-type microorganism (wild-type strain), methods using an auxotrophic strain derived from a wild-type strain, methods using a metabolic regulation mutant strain derived as a mutant strain resistant to any of various drugs from a wild-type strain, and methods using a strain having characteristics as both an auxotrophic strain and metabolic regulation mutant strain.

Further, in recent years, microorganisms in which an L-amino acid-producing ability is improved by recombinant DNA techniques are used for the L-amino acid production. Examples of methods for improving an L-amino acid-producing ability of a microorganism include, for example, enhancing the expression of a gene coding for an L-amino acid biosynthetic enzyme (U.S. Pat. No. 5,168,056 and U.S. Pat. No. 5,776,736), and enhancing inflow of a carbon source into an L-amino acid biosynthesis system (U.S. Pat. No. 5,906,925).

The acpP gene is a gene coding for the acyl carrier protein (ACP) (Zhang Y, Cronan J E Jr., J Bacteriol., 1996 June; 178(12)3614-20). ACP is translated as inactive apo-ACP, then a cofactor 4'-phosphopantetheine is added to the serine residue at the position 36 (in the case of *Escherichia coli*) of apo-ACP by ACP synthase, and apo-ACP is thereby converted into active holo-ACP. The ACP protein plays an important role in the fatty acid biosyntheses of bacteria, and so forth. Specifically, in the fatty acid biosynthesis, ACP (holo-ACP) binds to a fatty acid chain via the 4'-phosphopantetheine group, thereby to carry the fatty acid chain The fabF gene is a gene coding for β-ketoacyl-ACP synthase II (Zhang Y, Cronan J E Jr., J Bacteriol., 1996 Jun; 178(12)3614-20). The β-ketoacyl-ACP synthase II is one of the fatty acid biosynthesis enzymes, and participates in extension of fatty acid chain. Specifically, β-ketoacyl-ACP synthase II catalyzes the reaction that generates a 3-oxoacyl-ACP (carbon number=n+2) from an acyl ACP (carbon number=n) and malonyl-ACP (EC 2.3.1.41).

In *Escherichia coli*, the genes that participate in the biosynthesis of fatty acid, including the acpP gene and fabF gene, exist as the yceD-rpmF-plsX-fabHDG-acpP-fabF gene cluster. The genes of this gene cluster are co-transcribed as several gene pairs (Zhang Y, Cronan J E Jr., J Bacteriol., 1996 June; 178(12)3614-20). For example, the acpP gene and the fabF gene are co-transcribed as the acpP-fabF operon. In addition, the fabF gene is also independently transcribed with its own promoter. Furthermore, the acpP gene may also be co-transcribed from the fabD gene and the fabG gene in the yceD-rpmF-plsX-fabHDG-acpP-fabF gene cluster.

However, relationship between the acpP and fabF genes, and L-amino acid production has not been previously reported.

SUMMARY OF THE INVENTION

It is an aspect of the present invention to develop a novel technique for improving an L-amino acid-producing ability of a bacterium, and thereby to provide a method for efficiently producing an L-amino acid.

It is an aspect of the present invention to provide a bacterium in which the ability to produce an L-amino acid can be improved by modifying the bacterium so that the expression of the acpP and fabF genes is reduced.

It is an aspect of the present invention to provide a method for producing an L-amino acid comprising:

culturing a bacterium belonging to the family Enterobacteriaceae and having an L-amino acid-producing ability in a medium so that an L-amino acid is produced and accumulates in the medium or cells of the bacterium; and collecting the L-amino acid from the medium or cells, wherein the bacterium has been modified so that the acpP-fabF operon is attenuated.

It is an aspect of the present invention to provide the method as described above, wherein an activity of a protein encoded by a gene of the acpP-fabF operon is reduced.

It is an aspect of the present invention to provide the method as described above, wherein the acpP-fabF operon is attenuated by attenuating the expression of a gene of the acpP-fabF operon.

It is an aspect of the present invention to provide the method as described above, wherein the expression of the gene of the acpP-fabF operon is attenuated by modifying an expression control sequence of the gene.

It is an aspect of the present invention to provide the method as described above, wherein the gene of the acpP-fabF operon comprises the acpP gene and/or the fabF gene.

It is an aspect of the present invention to provide the method as described above, wherein the gene of the acpP-fabF operon comprises the acpP gene and the fabF gene.

It is an aspect of the present invention to provide the method as described above, wherein the expression of the gene of the acpP-fabF operon is attenuated by replacing the cytosine at position −34 upstream relative to the translation initiation site of the acpP gene with another base.

It is an aspect of the present invention to provide the method as described above, wherein the base is adenine.

It is an aspect of the present invention to provide the method as described above, wherein the bacterium is a bacterium belonging to a genus selected from the group consisting of *Escherichia*, *Pantoea*, and *Enterobacter*.

It is an aspect of the present invention to provide the method as described above, wherein the bacterium is *Escherichia coli*.

It is an aspect of the present invention to provide the method as described above, wherein the L-amino acid is L-lysine.

It is a further aspect of the present invention to provide a method for producing L-lysine comprising:

culturing *Escherichia coli* having L-lysine-producing ability in a medium so that L-lysine is produced and accumulates in the medium or cells of the *Escherichia coli*; and
collecting L-lysine from the medium or cells,
wherein the expression of a gene of the acpP-fabF operon has been attenuated in the Escherichia coli by modifying an expression control sequence of the gene.

It is a further aspect of the present invention to provide a method for producing L-lysine comprising:
culturing *Escherichia coli* having L-lysine-producing ability in a medium so that L-lysine is produced and accumulates in the medium or cells of the *Escherichia coli*; and
collecting L-lysine from the medium or cells,
wherein the cytosine at position −34 upstream relative to the translation initiation site of the acpP gene has been replaced with another base in the *Escherichia coli*.

It is a further aspect of the present invention to provide a method for producing L-lysine comprising:
culturing *Escherichia coli* having L-lysine-producing ability in a medium so that L-lysine is produced and accumulates in the medium or cells of the *Escherichia coli*; and
collecting L-lysine from the medium or cells,
wherein the cytosine at position −34 upstream relative to the translation initiation site of the acpP gene has been replaced with adenine in the *Escherichia coli*.

DESCRIPTION OF THE PREFERRED EMBODIMENTS

Hereafter, the present invention will be explained in detail.

The method of the present invention is a method for producing an L-amino acid by culturing a bacterium belonging to the family Enterobacteriaceae and having an L-amino acid-producing ability in a medium to produce and accumulate an L-amino acid in the medium or cells of the bacterium, and collecting the L-amino acid from the medium or cells, wherein the bacterium has been modified so that the acpP-fabF operon is attenuated. The bacterium used for this method can also be referred to as "the bacterium of the present invention".

<1> Bacterium of the Present Invention

The bacterium of the present invention is a bacterium belonging to the family Enterobacteriaceae and having an L-amino acid-producing ability, and which has been modified so that the acpP-fabF operon is attenuated.

<1-1> Bacterium Having L-amino Acid-Producing Ability

In the present invention, a "bacterium having an L-amino acid-producing ability" refers to a bacterium having an ability to produce and accumulate an objective L-amino acid in a medium or cells of the bacterium to such a degree that the L-amino acid can be collected, when the bacterium is cultured in the medium. The bacterium having an L-amino acid-producing ability may be a bacterium that can accumulate the objective L-amino acid in a medium in an amount larger than that obtainable with a non-modified strain. Examples of a non-modified strain include wild-type strains and parent strains. The bacterium having an L-amino acid-producing ability may be a bacterium that can accumulate the objective L-amino acid in a medium in an amount of 0.5 g/L or more, or 1.0 g/L or more.

Examples of the L-amino acid can include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. The bacterium of the present invention can have an ability to produce a single kind of L-amino acid, or two or more kinds of L-amino acids.

The term "amino acid" can refer to an L-amino acid unless otherwise stated. Further, the L-amino acid to be produced may be a free compound, a salt thereof, or a mixture thereof. That is, in the present invention, the term "L-amino acid" can refer to an L-amino acid in a free form, a salt thereof, or a mixture of them unless otherwise stated. Examples of the salt will be described later.

Examples of bacteria belonging to the family Enterobacteriaceae include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax-.cgi?id=91347) can be used.

The *Escherichia* bacteria are not particularly limited, and examples thereof include those classified into the genus *Escherichia* according to the taxonomy known to those skilled in the field of microbiology. Examples of the *Escherichia bacterium* include, for example, those described in the work of Neidhardt et al. (Backmann B. J., 1996, Derivations and Genotypes of some mutant derivatives of *Escherichia coli* K-12, pp.2460-2488, Table 1, In F.D. Neidhardt (ed.), *Escherichia coli* and Salmonella Cellular and Molecular Biology, Second Edition, American Society for Microbiology Press, Washington, D.C.). Examples of the Escherichia bacterium include, for example, *Escherichia coli*. Specific examples of *Escherichia coli* include, for example, *Escherichia coli* W3110 (ATCC 27325) and *Escherichia coli* MG1655 (ATCC 47076) derived from the prototype wild-type strain, K-12 strain.

The *Enterobacter* bacteria are not particularly limited, and examples thereof include those classified into the genus *Enterobacter* according to classification known to a person skilled in the art of microbiology. Examples of the *Enterobacter bacterium* include, for example, Enterobacter agglomerans and Enterobacter aerogenes. Specific examples of Enterobacter agglomerans include, for example, the Enterobacter agglomerans ATCC 12287 strain. Specific examples of *Enterobacter aerogenes* include, for example, the *Enterobacter aerogenes* ATCC 13048 strain, NBRC 12010 strain (Biotechnol Bioeng., 2007, Mar. 27;98(2)340-348), and AJ110637 strain (FERM ABP-10955). Examples the *Enterobacter bacterium* also include, for example, the strains described in European Patent Application Laid-open (EP-A) No. 0952221. In addition, Enterobacter agglomerans also include some strains classified as *Pantoea agglomerans*.

The *Pantoea* bacteria are not particularly limited, and examples thereof include those classified into the genus *Pantoea* according to classification known to a person skilled in the art of microbiology. Examples of the *Pantoea* bacteria include, for example, *Pantoea ananatis, Pantoea stewartii, Pantoea agglomerans*, and *Pantoea citrea*. Specific examples of *Pantoea ananatis* include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), and SC17(0) strain (VKPM B-9246). Some strains of *Enterobacter agglomerans* were recently reclassified into *Pantoea agglomerans*, *Pantoea ananatis*, or *Pantoea stewartii* on the basis of nucleotide sequence analysis of 16S rRNA etc. (Int. J. Syst. Bacteriol., 43, 162-173 (1993)). The *Pantoea* bacteria can include those reclassified into the genus *Pantoea* as described above.

Examples of the Erwinia bacteria include Erwinia amylovora and Erwinia carotovora. Examples of the Klebsiella bacteria include Klebsiella planticola.

These strains are available from, for example, the American Type Culture Collection (Address: 10801 University Boulevard, Manassas, Va. 20110-2209, United States of America). That is, registration numbers are given to the respective strains, and the strains can be ordered by using these registration numbers (refer to http://www.atcc.org/). The registration numbers of the strains are listed in the catalogue of the American Type Culture Collection.

The bacterium can inherently have an L-amino acid-producing ability, or may be a bacterium modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of coryneform bacteria, Escherichia bacteria, and so forth (see "Amino Acid Fermentation", Gakkai Shuppan Center (Ltd.), 1st Edition, published May 30, 1986, pp.77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, L-amino acid analogue-resistant strain, or metabolic regulation mutant strain having an L-amino acid-producing ability can be obtained by subjecting a parent strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of the objective L-amino acid. An enzyme activity can be enhanced by, for example, modifying a bacterium so that the expression of a gene coding for the enzyme is enhanced. Methods for enhancing gene expression are described in WO00/18935, EP 1010755 A, and so forth. The detailed procedures for enhancing enzyme activity will be described later.

Further, an L-amino acid-producing ability can also be imparted or enhanced by reducing the activity of an enzyme that catalyzes a reaction branching away from the biosynthetic pathway of an objective L-amino acid, and as a result, generates a compound other than the objective L-amino acid. The enzyme that catalyzes such a reaction can include an enzyme involved in the decomposition of the objective amino acid. The method for reducing an enzyme activity will be described later.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability include, for example, a method of modifying a bacterium so that the bacterium has an increased activity or activities of one or more kinds of enzymes such as the L-glutamic acid biosynthesis enzymes. Examples of such enzymes include, but are not particularly limited to, glutamate dehydrogenase (gdhA), glutamine synthetase (glnA), glutamate synthetase (gltBD), isocitrate dehydrogenase (icdA), aconitate hydratase (acnA, acnB), citrate synthase (gltA), methylcitrate synthase (prpC), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are the names of the genes encoding the enzymes (the same shall apply to the same occasions hereafter). It is preferable to enhance the activity or activities of one or more kinds of enzymes such as, for example, glutamate dehydrogenase, citrate synthase, phosphoenol pyruvate carboxylase, and methylcitrate synthase.

Examples of strains belonging to the family Enterobacteriaceae and modified so that the expression of the citrate synthase gene, phosphoenolpyruvate carboxylase gene, and/or glutamate dehydrogenase gene are increased include those disclosed in EP 1078989 A, EP 955368 A, and EP 952221 A. Further, examples of strains belonging to the family Enterobacteriaceae and modified so that the expression of a gene of the Entner-Doudoroff pathway (edd, eda) is increased include those disclosed in EP 1352966 B.

Examples of methods for imparting or enhancing L-glutamic acid-producing ability also include, for example, a method of modifying a bacterium so that the bacterium has a reduced activity or activities of one or more enzymes that catalyze a reaction branching away from the biosynthesis pathway of L-glutamine to generate a compound other than L-glutamic acid. Examples of such enzymes include, but are not particularly limited to, isocitrate lyase (aceA), α-ketoglutarate dehydrogenase (sucA), phosphotransacetylase (pta), acetate kinase (ack), acetohydroxy acid synthase (ilvG), acetolactate synthase (ilvD), formate acetyltransferase (pfl), lactate dehydrogenase (ldh), alcohol dehydrogenase (adh), glutamate decarboxylase (gadAB), succinate dehydrogenase (sdhABCD), and 1-pyroline-5-carboxylate dehydrogenase (putA). It is a particular example to reduce or delete, for example, the α-ketoglutarate dehydrogenase activity.

Escherichia bacteria having a reduced α-ketoglutarate dehydrogenase activity or are deficient in the α-ketoglutarate dehydrogenase activity, and methods for obtaining them are described in U.S. Pat. Nos. 5,378,616 and 5,573,945. Further, methods for reducing or deleting the α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, 8,129,151, and WO2008/075483. Specific examples of *Escherichia* bacteria having a reduced α-ketoglutarate dehydrogenase activity or deficient in the α-ketoglutarate dehydrogenase activity include the following strains.

E. coli W3110sucA::Kmr
E. coli AJ12624 (FERM BP-3853)
E. coli AJ12628 (FERM BP-3854)
E. coli AJ12949 (FERM BP-4881)

E. coli W3110sucA::Kmr is a strain obtained by disrupting the sucA gene coding for α-ketoglutarate dehydrogenase of E. coli W3110. This strain is completely deficient in the α-ketoglutarate dehydrogenase activity.

Examples of L-glutamic acid-producing bacteria and parent strains which can be used to derive them also include *Pantoea* bacteria, such as the *Pantoea ananatis* AJ13355 strain (FERM BP-6614), *Pantoea ananatis* SC17 strain (FERM BP-11091), and *Pantoea ananatis*SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Further, examples of L-glutamic acid-producing bacteria and parent strains which can be used to derive them also include Pantoea bacteria having a reduced α-ketoglutarate dehydrogenase activity or deficient in the α-ketoglutarate dehydrogenase activity. Examples of such strains include the AJ13356 strain (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, they are referred to as *Pantoea ananatis* in this specification.

Furthermore, examples of L-glutamic acid-producing bacteria and parent strains which can be used to derive them also include *Pantoea* bacteria such as the Pantoea ananatis SC17sucA/RSFCPG+pSTVCB strain, *Pantoea ananatis* AJ13601 strain, *Pantoea ananatis*NP106 strain, and *Pantoea ananatis* NA1 strain. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain is a strain selected from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The AJ13601 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parent strains which can be used to derive them also include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains include, for example, the sucAsdhA double-deficient strain of Pantoea ananatis NA1 strain (Japanese Patent Laid-open (Kokai) No. 2010-041920).

Examples of L-glutamic acid-producing bacteria and parent strains which can be used to derive them also include auxotrophic mutant strains. Specific examples of auxotrophic mutant strains include, for example, *E. coli* VL334thrC+(VKPM B-8961, EP 1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC+ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parent strains which can be used to derive them also include strains having resistance to an aspartic acid analogue. Such strains can also be deficient in the α-ketoglutarate dehydrogenase activity. Specific examples of strains having resistance to an aspartic acid analogue and deficient in the α-ketoglutarate dehydrogenase activity include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

Examples of methods for imparting or enhancing L-glutamic acid-producing ability also include a method of modifying a bacterium so that the D-xylulose-5-phosphate phosphoketolase activity and/or the fructose-6-phosphate phosphoketolase activity are/is enhanced (Japanese Patent Laid-open (Kohyo) No. 2008-509661). Either one of the D-xylulose-5-phosphate phosphoketolase activity and the fructose-6-phosphate phosphoketolase activity may be enhanced, or both may be enhanced. In this specification, D-xylulose-5-phosphate phosphoketolase and fructose-6-phosphate phosphoketolase may be collectively referred to as phosphoketolase.

The D-xylulose-5-phosphate phosphoketolase activity means an activity for converting xylulose-5-phosphate into glycelaldehyde-3-phosphate and acetyl phosphate with consuming phosphoric acid to release one molecule of H2O. This activity can be measured by the method described by Goldberg, M. et al. (Methods Enzymol., 9, 515-520, 1996) or the method described by L. Meile (J. Bacteriol., 183: 2929-2936, 2001).

The fructose-6-phosphate phosphoketolase activity means an activity for converting fructose-6-phosphate into erythrose-4-phosphate and acetyl phosphate with consuming phosphoric acid to release one molecule of H2O. This activity can be measured by the method described by Backer, E. (Methods Enzymol., 5, 276-280, 1962) or the method described by L. Meile (J. Bacteriol., 183:2929-2936, 2001).

Examples of methods for imparting or enhancing L-glutamine-producing ability also include, for example, a method of enhancing the expression of the yhfK gene (WO2005/085419) or the ybjL gene (WO2008/133161), which is an L-glutamic acid secretion gene.

<L-Glutamine-Producing Bacteria>

Examples of methods for imparting or enhancing L-glutamine-producing ability include, for example, a method of modifying a bacterium so that the bacterium has an increased activity or activities of one or more kinds of enzymes such as the L-glutamine biosynthesis enzymes. Examples of such enzymes include, but not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP 1229121).

Examples of methods for imparting or enhancing L-glutamine-producing ability also include, for example, a method of modifying a bacterium so that the bacterium has a reduced activity or activities of one or more kinds of enzymes such as the enzymes that catalyze a reaction branching away from the biosynthesis pathway of L-glutamine to generate a compound other than L-glutamine. Examples of such enzymes include, but are not particularly limited to, glutaminase.

Specific examples of L-glutamic acid-producing bacteria and parent strains which can be used to derive them include a strain belonging to the genus *Escherichia* and having a mutant glutamine synthetase in which the tyrosine residue of the position 397 is replaced with another amino acid residue (U.S. Patent Published Application No. 2003/0148474).

<L-Proline-Producing Bacteria>

Examples of methods for imparting or enhancing L-proline-producing ability include, for example, a method of modifying a bacterium so that the bacterium has an increased activity or activities of one or more kinds of enzymes such as the L-proline biosynthesis enzymes. Examples of such enzymes include glutamate-5-kinase (proB), Y-glutamylphosphate reductase, and pyroline-5-carboxylate reductase (putA). For enhancing the activity of such an enzyme, for example, the proB gene coding for a glutamate kinase desensitized to feedback inhibition by L-proline (German Patent No. 3127361) is a particular example.

Examples of methods for imparting or enhancing L-glutamine-producing ability also include, for example, a method of modifying a bacterium so that the bacterium has a reduced activity of an enzyme involved in decomposition of L-proline. Examples of such an enzyme include proline dehydrogenase and ornithine aminotransferase.

Specific examples of L-proline-producing bacteria and parent strains which can be used to derive them include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPMB-8011), which is a 3,4-dehydroxyproline and azetidine-2-carboxylate resistant strain, and *E. coli* 702ilvA strain (VKPMB-8012), which is an ilvA gene-deficient strain of the 702 strain (EP 1172433).

<L-Threonine-Producing Bacteria>

Examples of methods for imparting or enhancing L-threonine-producing ability include, for example, a method of modifying a bacterium so that the bacterium has an increased activity or activities of one or more kinds of enzymes such as the L-threonine biosynthesis enzymes. Examples of such enzymes include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, particular examples include one or more kinds of enzymes selected from aspartokinase III, aspartate semialdehyde dehydrogenase, aspartokinase I, homoserine kinase, aspartate aminotransferase, and threonine synthase. Any of the genes coding for the L-threonine biosynthesis enzymes can be introduced into a bacterium having a reduced ability to decompose threonine. Examples of such a strain in which threonine decomposition is suppressed include, for example, the *E. coli* TDH6 strain, which is deficient in the threonine dehydrogenase activity (Japanese Patent Laid-open (Kokai) No. 2001-346578).

The activities of the L-threonine biosynthesis enzymes are inhibited by the end product, L-threonine. Therefore, to construct L-threonine-producing strains, it is preferred that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, expression of the threonine operon can be enhanced by removing the leader sequence or the attenuator in the attenuation region (refer to Lynn, S. P., Burton, W. S., Donohue, T. J., Gould, R. M., Gumport, R. L, and Gardner, J. F., J. Mol. Biol. 19459-69 (1987); WO02/26993; WO2005/049808; and WO2003/097839).

The native promoter of the threonine operon is present upstream of the threonine operon, and can be replaced with a non-native promoter (refer to WO98/04715). Also, the threonine operon may be constructed so that the threonine biosynthesis genes are expressed under control of the repressor and promoter of λ-phage (European Patent No. 0593792). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

It is preferred that the expression amount of the threonine operon that is modified so as to be desensitized to feedback inhibition by L-threonine as described above is increased in a host by increasing the copy number thereof or by ligating it to a potent promoter. The copy number can be increased by introducing a plasmid containing the threonine operon into the host. The copy number can also be increased by transferring the threonine operon to the genome of the host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include the rhtA gene (Res. Microbiol. 154:123-135 (2003)), rhtB gene (European Patent Laid-open No. 0994190), rhtC gene (European Patent Laid-open No. 1013765), yfiK gene, and yeaS gene (European Patent Laid-open No. 1016710). As for methods for imparting L-threonine resistance to a host, those described in European Patent Laid-open No. 0994190 and WO90/04636 can be referred to.

Specific examples of L-threonine-producing bacteria and parent strains which can be used to derive them include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Patent No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and *E. coli* VKPM B-5318 (EP 0593792 B).

The VKPM B-3996 strain is a strain obtained by introducing the plasmid pVIC40 into the TDH-6 strain. The TDH-6 strain has sucrose-assimilating ability and is deficient in the thrC gene, and the ilvA gene thereof has a leaky mutation. This VKPM B-3996 strain also has a mutation in the rhtA gene, which imparts resistance to high concentration of threonine or homoserine. The plasmid pVIC40 is a plasmid obtained by inserting the thrA*BC operon containing a mutant thrA gene coding for an aspartokinase-homoserine dehydrogenase I resistant to feedback inhibition by threonine and the wild-type thrBC genes into an RSF1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 of which the regulatory region of the threonine operon is replaced with the temperature-sensitive λ-phage CI repressor and PR promoter. The VKPM B-5318 strain was deposited at the Russian National Collection of Industrial Microorganisms (VKPM, 1 Dorozhny proezd., 1 Moscow 117545, Russia) on May 3, 1990 under the accession number of VKPM B-5318.

The thrA gene which encodes aspartokinase-homoserine dehydrogenase I of *E. coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene which encodes threonine synthase of *E. coli* has been elucidated (nucleotide numbers 3734 to 5020, GenBank accession NC_000913.2, gi: 49175990). The thrC gene is located between the thrB gene and the yaaX open reading frame on the chromosome of *E. coli* K-12. The thrA*BC operon containing a mutant thrA gene which codes for an aspartokinase-homoserine dehydrogenase I resistant to feedback inhibition by threonine and the wild-type thrBC genes can be obtained from the well-known plasmid pVIC40, which is present in the threonine-producing strain *E. coli* VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation that imparts resistance to high concentrations of threonine or homoserine is an A-for-G substitution at position -1 with respect to the ATG start codon (ABSTRACTS of the 17th International Congress of Biochemistry and Molecular Biology in conjugation with Annual Meeting of the American Society for Biochemistry and Molecular Biology, San Francisco, California August 24-29, 1997, abstract No. 457; EP 1013765 A).

The asd gene of *E. coli* has already been elucidated (nucleotide numbers 3572511 to 3571408, GenBank accession NC_000913.1, gi:16131307), and can be obtained by PCR (refer to White, T. J., et al., Trends Genet, 5:185-189, 1989) utilizing primers prepared on the basis of the nucleotide sequence of the gene. The asd genes of other microorganisms can also be obtained in a similar manner.

The aspC gene of *E. coli* has also already been elucidated (nucleotide numbers 983742 to 984932, GenBank accession NC_000913.1, gi:16128895), and can be obtained by PCR utilizing primers prepared on the basis of the nucleotide sequence of the gene. The aspC genes of other microorganisms can also be obtained in a similar manner.

<L-Lysine-Producing Bacteria>

Examples of methods for imparting or enhancing L-lysine-producing ability include, for example, a method of modifying a bacterium so that the bacterium has an increased activity or activities of one or more kinds of enzymes such as the L-lysine biosynthesis enzymes. Examples of such enzymes include, but not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP 1253195 A). It is preferable to enhance the activity or activities of one or more kinds of enzymes selected from, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. In addition, L-lysine-producing bacteria and parent strains which can be used to derive them can express an increased level of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Further, since dihydrodipicolinate synthase (dapA) is subject to feedback inhibition by L-lysine, a mutant dapA gene coding for a dihydrodipicolinate synthase desensitized to feedback inhibition by L-lysine may be used for enhancing the activity of this enzyme.

Examples of methods for imparting or enhancing L-lysine-producing ability also include, for example, a method of modifying a bacterium so that the bacterium has a reduced activity or activities of one or more kinds of enzymes such as the enzymes that catalyze a reaction branching away from the biosynthetic pathway of L-lysine to generate a compound other than L-lysine. Examples of such enzymes include, but are not particularly limited to, homoserine dehydrogenase, lysine decarboxylase (U.S. Pat. No. 5,827,698), and malic enzyme (WO2005/010175).

Examples of L-lysine-producing bacteria and parent strains which can be used to derive them also include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues include, but are not particularly limited to, oxalysine, lysine hydroxamate, S-(2-aminoethyll-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parent strains which can be used to derive them include *E. coli* AJ11442 (FERM BP-1543, NRRL B-12185, see U.S. Pat. No. 4,346,170) and *E. coli* VL611. In these strains, aspartokinase is desensitized to feedback inhibition by L-lysine. Specific examples of L-lysine-producing bacteria and parent strains which can be used to derive them also include *E. coli* AJIK01 (NITE BP-01520). The AJIK01 strain was designated *E. coli* AJ111046, and deposited at the independent administrative agency, National Institute of Technology and Evaluation, International Patent Organism Depositary (#120, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Specific examples of L-lysine-producing bacteria and parent strains which can be used to derive them also include the *E. coli* WC196 strain. The WC196 strain was bred by imparting AEC resistance to the W3110 strain, which was derived from *E. coli* K-12 (U.S. Pat. No. 5,827,698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Preferred examples of L-lysine-producing bacteria include *E. coli* WC196ΔcadAΔldc and *E. coli* WC196ΔcadAΔldc/pCABD2 (WO2006/078039). The *E. coli* WC196ΔcadAΔldc is a strain constructed from the WC196 strain by disrupting the cadA and ldcC genes coding for lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and coding for a dihydrodipicolinate synthase (DDPS) having a mutation for desensitization to feedback inhibition by L-lysine, a mutant lysC gene derived from *Escherichia coli* and coding for aspartokinase III having a mutation for desensitization to feedback inhibition by L-lysine, the dapB gene derived from *Escherichia coli* and coding for dihydrodipicolinate reductase, and the ddh gene derived from Brevibacterium lactofermentum and coding for diaminopimelate dehydrogenase.

<L-Arginine-Producing Bacteria>

Examples of methods for imparting or enhancing L-arginine-producing ability include, for example, a method of modifying a bacterium so that the bacterium has an increased activity or activities of one or more kinds of enzymes such as the L-arginine biosynthesis enzymes. Examples of such enzymes include, but are not particularly limited to, N-acetylglutamate synthase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene coding for a mutant N-acetylglutamate synthase desensitized to feedback inhibition by L-arginine by substitution for the amino acid residues corresponding to the positions 15 to 19 of the wild type enzyme (European Patent Laid-open No. 1170361) can preferably be used.

Specific examples of L-arginine-producing bacteria and parent strains which can be used to derive them include, for example, the E. coli 237 strain (VKPM B-7925) (U.S. Patent Published Application No. 2002/058315A1), derivative strains thereof introduced with the argA gene coding for a mutant N-acetyl glutamate synthase (Russian Patent Application No. 2001112869, EP 1170361 A1), E. coli 382 strain derived from the 237 strain and having an improved acetic acid-assimilating ability (VKPM B-7926, EP 1170358 A1), and E. coli 382ilvA+strain, which is a strain obtained from the 382 strain by introducing the wild-type ilvA gene from E. coli K-12 strain thereto. The E. coli strain 237 was deposited at the Russian National Collection of Industrial Microorganisms (VKPM, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The E. coli 382 strain was deposited at the Russian National Collection of Industrial Microorganisms (VKPM, 1 Dorozhny proezd., 1 Moscow 117545, Russia) on Apr. 10, 2000 under accession number of VKPM B-7926.

Examples of L-arginine-producing bacteria and parent strains which can be used to derive them also include strains having resistance to amino acid analogues, and so forth. Examples of such strains include Escherichia coli mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

<L-Citrulline-Producing Bacteria and L-Ornithine-Producing Bacteria>

The biosynthetic pathways of L-citrulline and L-ornithine are common to that of L-arginine. Therefore, an ability to produce L-citrulline and/or L-ornithine can be imparted or enhanced by increasing the activity or activities of N-acetylglutamate synthase (argA), N-acetylglutamyl phosphate reductase (argC), ornithine acetyltransferase (argJ), N-acetylglutamate kinase (argB), acetylornithine transaminase (argD), and/or acetylornithine deacetylase (argE) (WO2006/35831).

<L-Histidine-Producing Bacteria>

Examples of methods for imparting or enhancing L-histidine-producing ability include, for example, a method of modifying a bacterium so that the bacterium has an increased activity or activities of one or more kinds of enzymes such as the L-histidine biosynthesis enzymes. Examples of such enzymes include, but are not particularly limited to, ATP phosphoribosyltransferase (hisG), phosphoribosyl AMP cyclohydrolase (hill), phosphoribosyl-ATP pyrophosphohydrolase (hill), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene coding for ATP phosphoribosyltransferase (hisG) (Russian Patent Nos. 2003677 and 2119536).

Specific examples of L-histidine-producing bacteria and parent strains which can be used to derive them include, for example, strains belonging to the genus Escherichia, such as the E. coli 24 strain (VKPM B-5945, RU 2003677), E. coli NRRL B-12116 to B-12121 (U.S. Pat. No. 4,388,405), E. coli H-9342 (FERM BP-6675) and H-9343 (FERM BP-6676, U.S. Pat. No. 6,344,347), E. coli H-9341 (FERM BP-6674, EP 1085087), E. coli A180/pFM201 (U.S. Pat. No. 6,258,554), E. coli FERM P-5038 and FERM P-5048, which have been introduced with a vector carrying a DNA encoding an L-histidine-biosynthesis enzyme (Japanese Patent Laid-open (Kokai) No. 56-005099), E. coli strains introduced with a gene for amino acid transport (EP 1016710 A), and E. coli 80 strain, which has been imparted with resistance to sulfaguanidine, DL-1,2,4-triazole-3-alanine, and streptomycin (VKPM B-7270, Russian Patent No. 2119536).

<L-Cysteine-Producing Bacteria>

Examples of methods for imparting or enhancing L-cysteine-producing ability include, for example, a method of modifying a bacterium so that the bacterium has an increased activity or activities of one or more kinds of enzymes such as the L-cysteine biosynthesis enzymes. Examples of such enzymes include, but are not particularly limited to, serine acetyltransferase (cysE) and 3-phosphoglycerate dehydrogenase (serA). The serine acetyltransferase activity can be enhanced by, for example, introducing a mutant cysE gene coding for a mutant serine acetyltransferase resistant to feedback inhibition by cysteine into a bacterium. Such a mutant serine acetyltransferase is disclosed in, for example, Japanese Patent Laid-open (Kokai) No. 11-155571 and U.S. Patent Published Application No. 20050112731. Further, the 3-phosphoglycerate dehydrogenase activity can be enhanced by, for example, introducing a mutant serA gene coding for a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Further, examples of methods for imparting or enhancing L-cysteine-producing ability also include, for example, a method of modifying a bacterium so that the bacterium has a reduced activity or activities of one or more kinds of enzymes such as the enzymes that catalyze a reaction branching away from the biosynthesis pathway of L-cysteine to generate a compound other than L-cysteine. Examples of such enzymes include, for example, enzymes involved in decomposition of L-cysteine. Examples of the enzymes involved in decomposition of L-cysteine include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), O-acetylserine sulfhydrylase B (cysM, Japanese Patent Laid-open (Kokai) No. 2005-245311), the malY gene product (Japanese Patent Laid-open (Kokai) No. 2005-245311), and the d0191 gene product of Pantoea ananatis (Japanese Patent Laid-open (Kokai) No. 2009-232844).

Further, examples of methods for imparting or enhancing L-cysteine-producing ability also include, for example, a method of enhancing the L-cysteine excretory system, and a method of enhancing the sulfate/thiosulfate transport system. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojlH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysPTWAM gene cluster.

Specific examples of L-cysteine-producing bacteria and parent strains which can be usd to derive them include, for example, E. coli JM15 transformed with different cysE alleles coding for feedback-resistant serine acetyltransferases (U.S. Pat. No. 6,218,168, Russian patent application 2003121601), E. coli W3110 having an over-expressed gene encoding a protein suitable for secretion of a cytotoxic substance (U.S. Pat. No. 5,972,663), E. coli strains having a reduced cysteine desulfohydrase activity (JP11155571A2), and E. coli W3110 having an increased activity of a positive transcriptional regulator for cysteine regulon encoded by the cysB gene (WO0127307A1).

<L-Methionine-Producing Bacteria>

Examples of L-methionine-producing bacteria and parent strains which can be used to derive them include L-threonine auxotrophic strains and mutant strains resistant to norleucine (Japanese Patent Laid-open (Kokai) No. 2000-139471). Examples of L-methionine-producing bacteria and parent strains which can be used to derivie them also include a strain containing a mutant homoserine transsuccinylase resistant to feedback inhibition by L-methionine (Japanese Patent Laid-open (Kokai) No. 2000-139471, U.S. Patent Published Application No. 20090029424). Since L-methionine is biosynthesized via L-cysteine as an intermediate, L-methionine-producing ability can also be improved by improving L-cysteine-producing ability (Japanese Patent Laid-open (Kokai) No. 2000-139471, U.S. Patent Published Application No. 20080311632).

Specific examples of L-methionine-producing bacteria and parent strains which can be used to derive them include, for example, E. coli AJ11539 (NRRL B-12399), E. coli AJ11540 (NRRL B-12400), E. coli AJ11541 (NRRL B-12401), E. coli AJ11542 (NRRL B-12402, British Patent No. 2075055), the E. coli 218 strain (VKPM B-8125, Russian Patent No. 2209248) and the 73 strain (VKPM B-8126, Russian Patent No. 2215782), which are resistant to norleucine, which is an analogue of L-methionine, and E. coli AJ13425 (FERMP-16808, Japanese Patent Laid-open (Kokai) No. 2000-139471). The AJ13425 strain is an L-threonine auxotrophic strain derived from the E. coli W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability include, for example, a method of modifying a bacterium so that the bacterium has an increased activity or activities of one or more kinds of enzymes such as the L-leucine biosynthesis enzymes. Examples of such enzymes include, but are not particularly limited to, the enzymes encoded by the genes of the leuABCD operon. Further, for enhancing the activity of such an enzyme, for example, the mutant leuA gene coding for an isopropyl maleate synthase desensitized to feedback inhibition by L-leucine (U.S. Pat. No. 6,403,342) can be preferably used.

Specific examples of L-leucine-producing bacteria and parent strains which can be used to derive them include, for example, strains belonging to the genus Escherichia, such as E. coli strains resistant to leucine (for example, the 57 strain (VKPM B-7386, U.S. Pat. No. 6,124,121)), E. coli strains resistant to an leucine analogue such as B-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), E. coli strains obtained by a gene engineering technique described in WO96/06926, and E. coli H-9068 (Japanese Patent Laid-open (Kokai) No. 8-70879).

<L-Isoleucine-Producing Bacteria>

Examples of methods for imparting or enhancing L-isoleucine-producing ability include, for example, a method of modifying a bacterium so that the bacterium has increased activity or activities of one or more enzymes such as the L-isoleucine biosynthesis enzymes. Examples of such enzymes include, but are not particularly limited to, threonine deaminase and acetohydroxy acid synthase (Japanese Patent Laid-open (Kokai) No. 2-458, FR 0356739, U.S. Pat. No. 5,998,178).

Specific examples of L-isoleucine-producing bacteria and parent strains which can be used to derive them include, for example, Escherichia bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

<L-Valine-Producing Bacteria>

Examples of methods for imparting or enhancing L-valine-producing ability include, for example, a method of modifying a bacterium so that the bacterium has an increased activity or activities of one or more kinds of enzymes such as the L-valine biosynthesis enzymes. Examples of such enzymes include, but are not particularly limited to, the enzymes encoded by the genes of the ilvGMEDA operon and the enzymes encoded by the ilvBNC operon. The ilvBN gene codes for acetohydroxy acid synthase, and the ilvC gene codes for isomeroreductase (WO00/50624). Expressions of the ilvGMEDA operon and the ilvBNC operon are suppressed (attenuated) by L-valine, L-isoleucine, and/or L-leucine. Therefore, for enhancing the activity of such an enzyme, it is preferred that the suppression of expression by the produced L-valine is released by removing or modifying a region required for the attenuation. Further, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, for L-valine production, it is preferred that the ilvA gene is, for example, disrupted, and thereby the threonine deaminase activity is decreased.

Examples of methods for imparting or enhancing L-valine-producing ability also include, for example, a method of modifying a bacterium so that the bacterium has a reduced activity or activities of one or more kinds of enzymes such as the enzymes that catalyze a reaction branching away from the biosynthesis pathway of L-valine to generate a compound other than L-valine. Examples of such enzymes include, but are not particularly limited to, threonine dehydratase involved in the L-leucine synthesis, and the enzymes involved in the D-pantothenic acid synthesis (WO00/50624).

Specific examples of L-valine-producing bacteria and parent strains which can be used to derive them include, for example, E. coli strains modified so as to overexpress the ilvGMEDA operon (U.S. Pat. No. 5,998,178).

Examples of L-valine-producing bacteria and parent strains which can be used to derive them also include mutant strains having a mutation in amino-acyl t-RNA synthetase (U.S. Pat. No. 5,658,766). Examples of such strains include, for example, E. coli VL1970, which has a mutation in the ileS gene encoding isoleucine t-RNA synthetase. E. coli VL1970 was deposited at the Russian National Collection of Industrial Microorganisms (VKPM, 1 Dorozhny Proezd, 1 Moscow 117545, Russia) on Jun. 24, 1988 under the accession number of VKPM B-4411. Examples of L-valine-producing bacteria and parent strains which can be used to derive them also include mutant strains requiring lipoic acid for growth and/or lacking H+-ATPase (WO96/06926).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability include, for example, a method of modifying a bacterium so that the bacterium has an increased activity or activities of one or more enzymes such as the L-tryptophan, L-phenylalanine, and/or L-tyrosine biosynthesis enzymes.

Examples of enzymes common to the biosynthesis systems of these aromatic amino acids include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (European Patent No. 763127). The expressions of the genes coding for these enzymes are controlled by the tyrosine repressor (tyrR), and the activities of these enzymes may be enhanced by deleting the tyrR gene (European Patent No. 763127).

Examples of the L-tryptophan biosynthesis enzymes include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase includes a and B subunits encoded by the trpA and trpB genes, respectively. Since the anthranilate synthase is subject to feedback inhibition by L-tryptophan, a gene coding for this enzyme introduced with a mutation for desensitization to feedback inhibition may be used for enhancing the activity of that enzyme. Since the phosphoglycerate dehydrogenase is subject to feedback inhibition by L-serine, a gene coding for this enzyme introduced with a mutation for desensitization to feedback inhibition may be used for enhancing the activity of that enzyme. Further, by increasing the expression of the operon (ace operon) consisting of the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes coding for these enzymes introduced with a mutation for desensitization to feedback inhibition may be used for enhancing the activities of these enzymes.

Examples of the L-tyrosine biosynthesis enzymes include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes coding for these enzymes introduced with a mutation for desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Further, the L-tryptophan, L-phenylalanine, and/or L-tyrosine-producing bacteria may be modified so that a by-product uptake system is enhanced. Examples of the by-product include aromatic amino acids other than the objective aromatic amino acid. Examples of the gene coding for such a by-product uptake system include, for example, tnaB and mtr, which are genes coding for the L-tryptophan uptake system, pheP, which is a gene coding for the L-phenylalanine uptake system, and tyrP, which is a gene coding for the L-tyrosine uptake system (EP 1484410).

Specific examples of L-tryptophan-producing bacteria and parent strains which can be used to derive them include, for example, E. coli JP4735/pMU3028 (DSM10122) and JP6015/pMU91 (DSM10123), which have a mutant trpS gene coding for a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient tryptophanase (U.S. Pat. No. 4,371,614), E. coli AGX17/pGX50,pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (U.S. Patent Published Applications 2003/0148473 A1 and 2003/0157667 A1).

Specific examples of L-phenylalanine-producing bacteria and parent strains which can be used to derive them include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutant pheA34 gene coding for a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of L-phenylalanine-producing bacteria and parent strains which can be used to derive them also include, for example, E. coli K-12 <W3110(tyrA)/pPHAB>(FERM BP-3566), E. coli K-12 <W3110(tyrA)/pPHAD>(FERM BP-12659), E. coli K-12 <W3110(tyrA)/pPHATerm>(FERM BP-12662), and E. coli K-12 AJ12604 <W3110(tyrA)/pBR-aroG4, pACMAB> (FERM BP-3579), which contains a gene coding for a chorismate mutase-prephenate dehydratase desensitized to feedback inhibition (EP 488424 B1). Specific examples of L-phenylalanine-producing bacteria and parent strains which can be used to derive them further include, for example, strains belonging to the genus Escherichia having an increased activity of the protein encoded by the yedA gene or the yddG gene (U.S. Patent Published Applications Nos. 2003/0148473 and 2003/0157667, WO03/044192).

Further, examples of methods for imparting or enhancing an L-amino acid-producing ability include, for example, a method of modifying a bacterium so that the bacterium has an increased activity for secreting an L-amino acid from a bacterial cell. Such an activity for secreting an L-amino acid can be increased by, for example, increasing the expression of a gene coding for a protein responsible for secretion of the L-amino acid. Examples of genes coding for the proteins responsible for secretion of various amino acids include, for example, b2682 gene (ygaZ), b2683 gene (ygaH), b1242 gene (ychE), and b3434 gene (yhgN) (Japanese Patent Laid-open (Kokai) No. 2002-300874).

Further, examples of methods for imparting or enhancing an L-amino acid-producing ability also include, for example, a method of modifying a bacterium so that the bacterium has an increased activity or activities of one or more proteins such as proteins involved in the glycometabolism and proteins involved in the energy metabolism.

Examples of the proteins involved in the glycometabolism include proteins involved in uptake of saccharides and the glycolysis system enzymes. Examples of genes coding for a protein involved in the glycometabolism include glucose-6-phosphate isomerase gene (pgi, WO01/02542), phosphoenolpyruvate synthase gene (pps, European Patent Laid-open No. 877090), phosphoenolpyruvate carboxylase gene (ppc, WO95/06114), pyruvate carboxylase gene (pyc, WO99/18228, European Patent Laid-open No. 1092776), phosphoglucomutase gene (pgm, WO03/04598), fructose bisphosphate aldolase gene (pfkB, fbp, WO03/04664), pyruvate kinase gene (pykF, WO03/008609), transaldolase gene (talB, WO03/008611), fumarase gene (fum, WO01/02545), non-PTS sucrose uptake gene (csc, European Patent Laid-open No. 149911), and sucrose assimilation gene (scrAB operon, WO90/04636).

Examples of genes encoding the proteins involved in the energy metabolism include the transhydrogenase gene (pntAB, U.S. Pat. No. 5,830,716) and cytochrome bo-type oxidase gene (cyoB, European Patent Laid-open No. 1070376).

The genes used for the breeding of the aforementioned L-amino acid-producing bacteria are not limited to the genes exemplified above and genes having a known nucleotide sequence, and may be a variant thereof, so long as it's original function is maintained. For example, the genes used for the breeding of the L-amino acid-producing bacteria may be a gene coding for a protein having an amino acid sequence of a known protein, but that includes substitution, deletion, insertion, or addition of one or several amino acid residues at one or several positions. For the variants of genes and proteins, the descriptions for variants of the acpP and fabF genes, and the proteins encoded thereby mentioned later can be applied, mutatis mutandis.

<1-2> Attenuation of acpP-fabF operon

The bacterium of the present invention has been modified so that the acpP-fabF operon is attenuated. The acpPfabFoperon participates in the biosynthesis of fatty acid (Zhang Y, Cronan J E Jr., J Bacteriol., 1996 Jun; 178(12):3614-20). Hence, it is presumed that when L-amino acid production culture is performed by using a bacterium in which the acpP fabF operon has been attenuated, inflow of a carbon source into the biosynthesis pathway of fatty acid is decreased, and as a result, surplus carbon source and surplus reducing power can be used for L-amino acid production thereby to improve L-amino acid production, as compared to when L-amino acid production culture is performed by using a non-modified strain. The bacterium of the present invention can be obtained by modifying a bacterium having an L-amino acid-producing ability so that the acpP-fabF operon is attenuated. Further, the bacterium of the present invention can also be obtained by modifying a bacterium so that the acpP-fabF operon is attenuated, and then imparting an L-amino acid producing ability to the bacterium or enhancing L-amino acid-producing ability of the bacterium. The bacterium of the present invention may also be a bacterium that has acquired an L-amino acid-producing ability by being modified so that the acpP-fabF operon is attenuated. The modifications for constructing the bacterium of the present invention can be performed in an arbitrary order.

The expression that "the acpP-fabF operon is attenuated" means that the activity of a protein encoded by a gene of the acpP-fabF operon is reduced, and/or that the expression of a gene of the acpPfabFoperon is reduced. The expression that "the expression of a gene is reduced" means that the transcription amount of the gene (the amount of mRNA) is reduced, and/or that the translation amount of the gene (the amount of the protein) is reduced. The "gene of the acpP-fabF operon" means the acpP gene and/or the fabF gene. That is, the "protein encoded by a gene of the acpP-fabF operon" refers to a protein encoded by the fabF gene and/or a protein encoded by the acpP gene, i.e. AcpP protein and/or FabF protein. The activity of a protein can be reduced by, for example, attenuating the expression of a gene coding for the protein, or disrupting a gene coding for the protein, as described later. That is, the expression that "the acpP-fabF operon is attenuated" may also mean that, for example, the expression of a gene of the acpP-fabF operon is attenuated. In the present invention, for example, the expression of either one or both of the acpP gene and the fabF gene may be attenuated. That is, the expression of the entire acpP-fabF operon may also be attenuated.

The acpP gene encodes for the acyl carrier protein (ACP). "ACP" is a protein having a function of binding with a fatty acid chain via the 4'-phosphopantetheine group, and thereby carrying the fatty acid chain at the time of fatty acid biosynthesis. This function is also referred to as the "ACP activity". ACP is translated as an inactive apo-ACP, then 4'-phosphopantetheine as a cofactor is added to the serine residue at position 36 (in the case of Escherichia coli) of apo-ACP by the ACP synthase, and apo-ACP is thereby made into active holo-ACP.

The fabF gene encodes for β-ketoacyl-ACP synthase II. The "β-ketoacyl-ACP synthase II" refers to an enzyme that catalyzes the reaction that generates a 3-oxoacyl-ACP (carbon number=n+2) from an acyl-ACP (carbon number=n) and malonyl-ACP (EC 2.3.1.41). The activity of catalyzing this reaction is also referred to as the "β-ketoacyl-ACP synthase II activity".

The acpP gene of the *Escherichia coli* K-12 MG1655 strain corresponds to the sequence of the positions 1150838 to 1151074 in the genome sequence registered at the NCBI database as GenBank accession NC_000913 (VERSION NC_000913.2 GI: 49175990). The acpP gene of the MG1655 strain is synonymous with ECK1080 and JW1080. Further, the AcpP protein of the MG1655 strain is registered as GenBank accession NP_415612 (version NP_415612.1 GI: 16129057, locus_tag"b 1094").

The fabF gene of the *Escherichia coli* K-12 MG1655 strain corresponds to the sequence of the positions 1151162 to 1152403 in the genome sequence registered at the NCBI database as GenBank accession NC_000913 (VERSION NC_000913.2 GI: 49175990). The fabF gene of the MG1655 strain is synonymous with ECK1081 and JW1081. Further, the FabF protein of the MG1655 strain is registered as GenBank accession NP_415613 (version NP_415613.1 GI: 16129058, locus_tag"b 1095").

The nucleotide sequence of the acpP-fabF operon (including upstream 210 by thereof) of the MG1655 strain is shown as SEQ ID NO: 7. In SEQ ID NO: 7, the nucleotide sequence of the acpP gene corresponds to the positions 211 to 447, and the nucleotide sequence of the fabF gene corresponds to the positions 535 to 1776. Further, the amino acid sequences of the AcpP protein and FabF protein of the MG1655 strain are shown as SEQ ID NOS: 8 and 9, respectively.

The acpP gene of the *Pantoea ananatis* AJ13355 strain corresponds to the sequence of the positions 986154 to 986528 in the genome sequence registered at the NCBI database as GenBank accession NC_017531 (VERSION NC_017531.1 GI: 386014600). Further, the AcpP protein of the AJ13355 strain is registered as GenBank accession YP_005933706 (version YP_005933706.1 GI: 386015425).

The fabF gene of the *Pantoea ananatis* AJ13355 strain corresponds to the sequence of the positions 986650 to 987855 in the genome sequence registered at the NCBI database as GenBank accession NC_017531 (VERSION NC_017531.1 GI: 386014600). Further, the FabF protein of the AJ13355 strain is registered as GenBank accession YP_005933707 (version YP_005933707.1 GI: 386015426).

The nucleotide sequence of the acpP-fabF operon (including upstream 210 by thereof) of the AJ13355 strain is shown as SEQ ID NO: 10. In SEQ ID NO: 10, the nucleotide sequence of the acpP gene corresponds to the positions 211 to 585, and the nucleotide sequence of the fabF gene corresponds to the positions 707 to 1912. Further, the amino acid sequences of the AcpP protein and the FabF protein of the AJ13355 strain are shown as SEQ ID NOS: 11 and 12, respectively.

The AcpP protein or FabF protein may be a variant of the aforementioned AcpP protein or FabF protein, so long as the original function of each protein is maintained. Similarly, the acpP gene or fabF gene may be a variant of the aforementioned acpP gene or fabF gene, so long as the original function of each gene is maintained. Such a variant of which the original function is maintained may also be called "conservative variant". The term "AcpP protein" or "FabF protein" is not limited to the aforementioned AcpP protein or FabF protein, but also includes conservative variants thereof. Similarly, the term "acpP gene" or "fabF gene" is not limited to the aforementioned acpP gene or fabF gene, but also includes conservative variants thereof. Examples of such a conservative variant include, for example, homologues and artificially modified variants of the aforementioned AcpP protein or FabF protein, or of the aforementioned acpP gene or fabF gene.

The expression that "the original function of the protein is maintained" means that a variant of the protein or the gene has a function (i.e. activity or property) corresponding to the function (i.e. activity or property) of the original protein or the original gene. Namely, for example, the expression that "the original function of the protein is maintained" used for the AcpP protein means that the protein has the ACP activity, and the expression that "the original function of the protein is maintained" used for the FabF protein means that the protein has the β-ketoacyl-ACP synthase II activity. Also, for example, the expression that "the original function of the gene is maintained" used for the acpP gene means that the gene encodes a protein having the ACP activity, and the expression that "the original function of the gene is maintained" used for the fabF gene means that the gene encodes a protein having the β-ketoacyl-ACP synthase II activity.

A gene coding for a homologue of the aforementioned AcpP protein or FabF protein is easily obtained from a public database by, for example, BLAST search or FASTA search using any of the aforementioned nucleotide sequences of the acpP gene or fabF gene as a query sequence. Further, a gene coding for a homologue of the aforementioned AcpP protein or FabF protein can be obtained by, for example, PCR using the chromosome of an organism such as a bacterium as the template, and oligonucleotides prepared on the basis of a known gene sequence thereof as primers.

The acpP gene or fabF gene may be a gene coding for a conservative variant of the aforementioned AcpP protein or FabF protein. For example, the acpP gene or fabF gene may be, for example, a gene coding for a protein having any of the aforementioned amino acid sequences (for example, the amino acid sequence of SEQ ID NO: 8, 9, 11, or 12) including substitution, deletion, insertion or addition of one or several amino acid residues at one or several positions, so long as it codes for a protein having the original function. In such a case, usually 70% or more, 80% or more, or 90% or more, of the corresponding activity of the protein (i.e. the ACP activity or the β-ketoacyl-ACP synthase II activity) can be maintained with respect to the protein not including addition, deletion, insertion or addition of one or several amino acid residues. Although the number of "one or several" may differ depending on the positions of amino acid residues in the three-dimensional structure of the protein or types of amino acid residues, specifically, it can be 1 to 50, 1 to 40, 1 to 30, 1 to 20, 1 to 10, 1 to 5, or 1 to 3.

The aforementioned substitution, deletion, insertion, or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

Furthermore, the gene having such a conservative mutation as mentioned above may be a gene coding for a protein showing a homology of 80% or more, 90% or more, 95% or more, 97% or more, or 99% or more, to the total amino acid sequence of any of the amino acid sequences mentioned above, and having the original function. In this specification, "homology" means "identity".

Further, the acpP gene or fabF gene may be a DNA that is able to hybridize with a probe that can be prepared from a known gene sequence, such as a sequence complementary to the whole or a part of any of the aforementioned nucleotide sequences (for example, nucleotide sequences of the positions 211 to 447 of SEQ ID NO: 7, the positions 535 to 1776 of SEQ ID NO: 7, the positions 211 to 585 of SEQ ID NO: 10, or the positions 707 to 1912 of SEQ ID NO: 10), under stringent conditions, and codes for a protein having the original function. Further, the acpP-fabF operon may be a DNA that is able to hybridize with a probe that can be prepared from a known gene sequence, such as a sequence complementary to the whole or a part of any of the aforementioned nucleotide sequences (for example, total nucleotide sequence of SEQ ID NO: 7, nucleotide sequence of the positions 211 to 1776 of SEQ ID NO: 7, total nucleotide sequence of SEQ ID NO: 10, or nucleotide sequence of the positions 211 to 1912 of SEQ ID NO: 10), under stringent conditions, and codes for a protein having the original function. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

As described above, the probe used for the aforementioned hybridization may be a part of a sequence that is complementary to the aforementioned gene. Such a probe can be prepared by PCR using oligonucleotides prepared on the basis of a known gene sequence as primers and a DNA fragment containing any of the nucleotide sequences as a template. As the probe, for example, a DNA fragment having a length of about 300 by can be used. When a DNA fragment having a length of about 300 by is used as the probe, the washing conditions of the hybridization may be, for example, 50° C., 2×SSC and 0.1% SDS.

Further, in the acpP gene or fabF gene, an arbitrary codon may be replaced with an equivalent codon, so long as the gene codes for a protein having the original function. For example, the acpP gene or fabF gene may be modified so that it has optimal codons according to codon frequencies observed in a host to be used.

The above descriptions concerning variants of the genes and proteins can also be applied mutatis mutandis to arbitrary proteins such as L-amino acid biosynthesis enzymes and genes coding for them.

<1-3> Method for Reducing Activity of Protein

Hereafter, methods for reducing the activity of a protein such as the AcpP protein and the FabF protein will be explained.

The expression "the activity of a protein is reduced" means that the activity of the protein per cell is decreased as compared with that of a non-modified strain such as a wild-type strain or parent strain, and includes a state that the activity has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may mean the transcription amount of a gene (the amount of mRNA) coding for the protein or the translation amount of the protein (the amount of the protein). The state that "the number of molecules of the protein per cell is reduced" includes a state that the protein does not exist at all. The state that "the function of each molecule of the protein is reduced" includes a state that the function of each protein molecule completely disappears. Although the degree of the reduction in the activity of a protein is not particularly limited so long as the activity is reduced as compared with that of a non-modified strain, it may be reduced to, for example, 90% or less, 80% or less, 70% or less, 60% or less, 55% or less, 50% or less, 30% or less, 20% or less, 10% or less, 5% or less, or 0% of that of a non-modified strain.

The modification for reducing the activity of a protein can be attained by, for example, reducing the expression of a gene coding for the protein. The state that "the expression of a gene is reduced" includes a state that the gene is not expressed at all. The state that "the expression of a gene is reduced" is also referred to as "the expression of a gene is attenuated". The expression of a gene may be reduced to 90% or less, 80% or less, 70% or less, 60% or less, 55% or less, 50% or less, 30% or less, 20% or less, 10% or less, 5% or less, or 0% of that of a non-modified strain.

In addition, it is known that, for example, in E. coli, the acpP gene is indispensable (essential). Therefore, when the activity of the AcpP protein is reduced, the activity of the AcpP protein is made to remain to such an extent that, when the bacterium of the present invention is cultured in a medium, the bacterium of the present invention can proliferate, and an objective L-amino acid is produced. That is, the activity of the AcpP protein shall not be reduced to 0% of that of a non-modified strain. For example, 1% or more, 5% or more, 10% or more, 15% or more, 17% or more, 20% or more, 30% or more, or 50% or more of the activity of the AcpP protein may be remained as compared with that of a non-modified strain. Specifically, the activity of the AcpP protein may also be reduced to, for example, 1% to 90%, 5% to 80%, 10% to 70%, 15% to 60%, or 17% to 55% of that of a non-modified strain. Further, the expression amount of the acpP gene shall not be reduced to 0% of that of a non-modified strain. For example, 1% or more, 5% or more, 10% or more, 15% or more, 17% or more, 20% or more, 30% or more, or 50% or more of the expression amount of the acpP gene may be remained as compared with that of a non-modified strain. Specifically, the expression amount of the acpP gene may also be reduced to, for example, 1% to 90%, 5% to 80%, 10% to 70%, 15% to 60%, or 17% to 55% of that of a non-modified strain. Such descriptions concerning the case where the activity of the AcpP protein is reduced may also be applied mutatis mutandis to a case where the activity of the FabF protein is reduced.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and a spacer region between RBS and the start codon. It is known that the AcpP protein is an abundant protein in the cells, and hence, it is suggested that the wild-type promoter of the acpP gene shows a high activity (Zhang Y, Cronan J E Jr., J Bacteriol., 1996 Jun; 178(12)3614-20). Therefore, the expression of the acpP gene can be reduced by, for example, replacing the wild-type promoter of the acpP gene with a promoter that shows a weaker activity. Examples of the promoter that shows a weaker activity than the wild-type promoter of the acpP gene include, for example, lac promoter and $P_{tac84}$ promoter disclosed in Russian Patent Published Application No. 2006/134574. When an expression control sequence is modified, one or more nucleotides, two or more nucleotides, or three or more nucleotides, of the expression control sequence can be modified. Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Further, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Further, for example, the gene expression itself may be reduced by disruption of a gene as described later.

The acpP gene and the fabF gene are co-transcribed as the acpP-fabF operon. The fabF gene is also independently transcribed with its own promoter. Further, the acpP gene may also be co-transcribed from the fabD gene and fabG gene in the yceD-rpmF-plsX-fabHDG-acpP-fabF gene cluster. Therefore, for example, by modifying the promoter that controls the co-transcription of the acpP-fabF operon, the total expression of the acpP gene and fabF gene may be reduced. Alternatively, for example, by modifying the own promoter of the fabF gene, the expression of the fabF gene may be independently reduced. Further, for example, by modifying the promoter of the fabD gene and/or the fabG gene, the expression of the acpP gene may be reduced together with the expression of the fabD gene and/or the fabG gene. Furthermore, for example, by introducing a mutation that reduces the expression of a gene into the coding region of the acpP gene and/or the fabF gene, the expression of the acpP gene and/or the fabF gene may be reduced.

Further, specific examples of the mutation that reduces the expression the acpP gene and/or the fabF gene include, for example, such a mutation that cytosine (C) at position −34 upstream of the translation initiation site of the acpP gene is replaced with another base. The other base can be adenine (A).

The phrase "position −34 upstream relative to the translation initiation site of the acpP gene" can mean the 34th position on the upstream side counted from A of the start codon (ATG) of the acpP gene in the nucleotide sequence shown as SEQ ID NO: 7. The position of A of the start codon (ATG) corresponds to the position +1, and the position next to that position on the upstream side is the position −1. In other words, the "position −34 upstream relative to the translation initiation site of the acpP gene" means a position corresponding to position 177 of the nucleotide sequence shown as SEQ ID NO: 7 (namely, the position 1150804 of the genome sequence of *Escherichia coli* K-12 MG1655 strain registered as GenBank accession NC_000913). The "position -34 upstream of the translation initiation site of the acpP gene" represents a relative position based on the sequence of SEQ ID NO: 7, and the absolute position may shift forward or backward due to deletion, insertion, addition, or the like of one or more nucleotides. That is, when one nucleotide is deleted in the sequence of SEQ ID NO: 7 between the nucleotide of the position 177 and A of the start codon, the "position −34 upstream of the translation initiation site of the acpP gene" means the 33th position on the upstream side counted from A of the start codon of the acpP gene. When one nucleotide is inserted in the sequence of SEQ ID NO: 7 between the nucleotide of the position 177 and A of the start codon, the "position -34 upstream of the translation initiation site of the acpP gene" means the 35th position on the upstream side counted from A of the start codon of the acpP gene.

Which nucleotide corresponds to the nucleotide of the "position −34 upstream of the translation initiation site of the acpP gene" can be determined in the acpP-fabF operon of an arbitrary bacterium by, for example, aligning the upstream sequence of the acpP gene of the bacterium and the upstream sequence of the acpP gene shown as SEQ ID NO: 7. Such alignment can be performed by, for example, using known gene analysis software. Specific examples of such software include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

The modification for reducing the activity of a protein can also be attained by, for example, disrupting a gene coding for the protein. Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein is reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272-8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of the objective substance.

Such modification of a gene on a chromosome as described above can be attained by, for example, preparing a deficient type gene in which a partial sequence of the gene is deleted so that it cannot produce a protein that can normally function, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is contained in the recombinant DNA, the operation becomes easy. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from A phage (Cho, E. H., Gumport, R. I., Gardner, J. F., J. Bacteriol., 1845200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

The modification for reducing the activity of a protein can also be attained by, for example, a mutagenesis treatment. Examples of the mutagenesis treatment include irradiation of X-ray, irradiation ultraviolet, and a treatment with a mutation agent such as N-methyl-N'- nitro-N-nitrosoguanidine (MNNG), ethyl methanesulfonate (EMS), and methyl methanesulfonate (MMS).

When a protein functions as a complex that includes a plurality of subunits, a part or all of the plurality of subunits may be modified, so long as the activity of the protein is eventually reduced. That is, for example, a part or all of a plurality of genes that code for the respective subunits may be disrupted or the like. Further, when there is a plurality of isozymes of a protein, a part or all of the activities of the plurality of isozymes may be reduced, so long as the activity of the protein is eventually reduced. That is, for example, a part or all of a plurality of genes that code for the respective isozymes may be disrupted or the like.

A reduction in the activity of a protein can be confirmed by measuring the activity of the protein.

A reduction in the activity of a protein can also be confirmed by confirming a reduction in the expression of a gene coding for the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA include Northern hybridization, RT-PCR, and so forth (Molecular Cloning, Cold spring Harbor Laboratory Press, Cold Spring Harbor (USA), 2001). The amount of mRNA may be decreased to, for example, 90% or less, 80% or less, 70% or less, 60% or less, 55% or less, 50% or less, 30% or less, 20% or less, 10% or less, 5% or less, or 0%, of that observed in a non-modified strain. However, the amount of mRNA transcribed from the acpP gene shall not be reduced to 0% of that of a non-modified strain. For example, when the expression of the acpP gene is reduced, the amount of mRNA that is transcribed from the gene that remains can be 1% or more, 5% or more, 10% or more, 15% or more, 17% or more, 20% or more, 30% or more, or 50% or more as compared with that observed in a non-modified strain. Specifically, when the expression of the acpP gene is reduced, the amount of mRNA transcribed from the acpP gene may be reduced to, for example, 1% to 90%, 5% to 80%, 10% to 70%, 15% to 60%, or 17% to 55% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein may be decreased to, for example, 90% or less, 80% or less, 70% or less, 60% or less, 55% or less, 50% or less, 30% or less, 20% or less, 10% or less, 5% or less, or 0%, of that observed in a non-modified strain. However, the amount of the AcpP protein shall not be reduced to 0% of that of a non-modified strain. For example, when the expression of the acpP gene is reduced, the amount of protein encoded by the gene that remains can be 1% or more, 5% or more, 10% or more, 15% or more, 17% or more, 20% or more, 30% or more, or 50% or more as compared with that observed in a non-modified strain. Specifically, when the expression of the acpP gene is reduced, the amount of the AcpP protein may be reduced to, for example, 1% to 90%, 5% to 80%, 10% to 70%, 15% to 60%, or 17% to 55% of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein can be applied to, besides the attenuation of the acpP-fabF operon, reduction in the activity of an arbitrary protein such as enzymes that catalyze a reaction branching away from the biosynthetic pathway of an objective L-amino acid to generate a compound other than the objective L-amino acid, and reduction in the expression of an arbitrary gene such as genes coding for those arbitrary proteins.

<1-4> Methods for Increasing Activity of Protein

Hereafter, methods for increasing the activity of a protein will be explained.

The expression "the activity of a protein is increased" means that the activity of the protein per cell is increased as compared with that of a non-modified strain such as a wild-type strain or a parent strain. The state that "the activity of a protein is increased" is also expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may mean the transcription amount of a gene (the amount of mRNA) coding for the protein, or the translation amount of the gene (the amount of the protein). Further, the state that "the activity of a protein is increased" includes not only a state that the activity of the objective protein is increased in a strain inherently having the activity of the objective protein, but also a state that the activity of an objective protein is imparted to a strain not inherently having the activity of the objective protein. Further, so long as the activity of the protein is eventually increased, the activity of the objective protein inherently present in a host may be reduced or eliminated, and then an appropriate type of the protein may be imparted thereto.

Although the degree of the increase in the activity of a protein is not particularly limited so long as the activity of the protein is increased as compared with a non-modified strain, the activity of the protein may be increased, for example, 1.5 times or more, 2 times or more, or 3 times or more, as compared with that of a non-modified strain. Further, when the non-modified strain does not have the activity of the objective protein, it is sufficient that the protein is produced by introducing the gene coding for the protein, and for example, the protein may be produced to such an extent that the enzyme activity can be measured.

The modification that increases the activity of a protein is attained by, for example, increasing the expression of a gene coding for the protein. The state that "the expression of a gene is increased" is also referred to as "the expression of a gene is enhanced". The expression of a gene may be increased 1.5 times or more, 2 times or more, or 3 times or more, as compared with that observed in a non-modified strain. Further, the state that "the expression of a gene is increased" includes not only a state that the expression amount of a target gene is increased in a strain that inherently expresses the target gene, but also a state that the gene is introduced into a strain that does not inherently express the target gene, and expressed therein. That is, the phrase "the expression of a gene is increased" also means, for example, that the target gene is introduced into a strain that does not have the gene, and expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for production of the objective substance as a target. Homologous recombination can be performed by, for example, a method of using a linear DNA such as Red-driven integration (Datsenko, K. A., and Wanner, B. L., Proc. Natl. Acad. Sci. USA, 97:6640-6645 (2000)), a method of using a plasmid having a temperature sensitive replication origin, a method of using a plasmid capable of conjugative transfer, a method of using a suicide vector not having a replication origin that functions in a host, or a transduction method using a phage. Further, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Further, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment including the target gene can be obtained by, for example, PCR using the genomic DNA of a microorganism having the target gene as the template. As the vector, a vector autonomously replicable in the cell of the host can be used. The vector can be a multi-copy vector. Further, the vector can have a marker such as an antibiotic resistance gene for selection of transformant. Further, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in bacteria belonging to the family Enterobacteriaceae such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), and broad host-range vector RSF1010.

When a gene is introduced, it is sufficient that the gene can be expressed by the bacterium of the present invention. Specifically, it is sufficient that the gene is introduced so that it is expressed under the control by a promoter sequence that functions in the bacterium of the present invention. The promoter may be a promoter derived from the host, or a heterogenous promoter. The promoter may be the native promoter of the gene to be introduced, or a promoter of another gene. As the promoter, for example, such a stronger promoter as mentioned later may also be used. Further, for example, a terminator for termination of gene transcription may be located downstream of the gene. The terminator is not particularly limited so long as it functions in in the bacterium of the present invention. The terminator may be a terminator derived from the host, or a heterogenous terminator. The terminator may be the native terminator of the gene to be introduced, or a terminator of another gene. Specific examples of a terminator include, for example, T7 terminator, T4 terminator, fd phage terminator, tet terminator, and trpA terminator. Vectors, promoters, and terminators available in various microorganisms are disclosed in detail in "Fundamental Microbiology Vol. 8, Genetic Engineering, KYORITSU SHUPPAN CO., LTD, 1987", and those can be used.

Further, when two or more of genes are introduced, it is sufficient that the each gene each can be expressed by the bacterium of the present invention. For example, all the genes may be carried by a single expression vector or a chromosome. Further, the genes may be separately carried by two or more expression vectors, or separately carried by a single or two or more expression vectors and a chromosome. An operon constituted by two or more genes may also be introduced.

The gene to be introduced is not particularly limited so long as it codes for a protein that functions in the host. The gene to be introduced may be a gene derived from the host, or may be a heterogenous gene. The gene to be introduced can be obtained by, for example, PCR using primers designed on the basis of the nucleotide sequence of the gene and the genomic DNA of an organism having the gene or a plasmid carrying the gene as a template. The gene to be introduced may also be totally synthesized, for example, on the basis of the nucleotide sequence of the gene (Gene, 60(1), 115-127 (1987)).

In addition, when a protein functions as a complex that includes a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that code for the subunits may be enhanced. It is usually preferable to enhance the expression of all of the plurality of genes coding for the subunits. Further, the subunits constituting the complex may be derived from a single kind of organism or two or more kinds of organisms, so long as the complex has a function of the objective protein. That is, for example, genes of the same organism coding for a plurality of subunits may be introduced into a host, or genes of different organisms coding for a plurality of subunits may be introduced into a host.

Further, the expression of a gene can be increased by improving the transcription efficiency of the gene. The transcription efficiency of a gene can be improved by, for example, replacing the promoter of the gene on a chromosome with a stronger promoter. The "stronger promoter" means a promoter that provides improved transcription of a gene compared with the native or existing wild-type promoter of the gene. Examples of stronger promoters include, for example, the known high expression promoters such as T7 promoter, trp promoter, lac promoter, tac promoter, thr promoter, trc promoter, tet promoter, araBAD promoter, rpoH promoter, PR promoter, and PL promoter. Further, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Further, the expression of a gene can also be increased by improving the translation efficiency of the gene. The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Further, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying these nucleotides.

In the present invention, sites that affect the gene expression, such as a promoter, SD sequence, and spacer region between RBS and the start codon, are also collectively called "expression control region". An expression control region can be identified by using a promoter search vector or gene analysis software such as GENETYX. Such an expression control region can be modified by, for example, a method of using a temperature sensitive vector or the Red driven integration method (WO2005/010175).

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess amount of rare codons, a translational problem may arise. According to recent research, it has been suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a synonymous, more frequently used codon. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database"(kazusa.or.jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of a protein can also be attained by, for example, enhancing the specific activity of the enzyme. Enhancement of the specific activity also includes reduction or elimination of feedback inhibition. A protein showing an enhanced specific activity can be obtained by, for example, searching various organisms. Further, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Further, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for Bacillus subtilis (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by measuring the increase in the expression of a gene coding for the protein. An increase in the expression of a gene can be measured by confirming an increase in the transcription amount of the gene, or by confirming an increase in the amount of a protein expressed from the gene.

An increase of the transcription amount of a gene can be confirmed by comparing the amount of mRNA transcribed from the gene with that observed in a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

The aforementioned methods for increasing the activity of a protein can be applied to enhancement of the activity of an arbitrary protein such as L-amino acid biosynthesis enzymes, and enhancement of the expression of an arbitrary gene such as genes coding for the those arbitrary proteins.

<2> Method for Producing L-amino Acid of the Present Invention

The method of the present invention is a method for producing an L-amino acid by culturing the bacterium of the present invention in a medium to produce and accumulate the L-amino acid in the medium or cells of the bacterium, and collecting the L-amino acid from the medium or the cells. In the present invention, a single kind of L-amino acid may be produced, or two or more kinds of L-amino acids may be produced.

The medium to be used is not particularly limited, so long as the bacterium of the present invention can proliferate in it, and an objective L-amino acid can be produced. As the medium, for example, a usual medium used for culture of microorganisms such as bacteria can be used. The medium may contain a carbon source, nitrogen source, phosphorus source, and sulfur source, as well as components selected from other various organic components and inorganic components, as required. Types and concentrations of the medium components can be appropriately set according to various conditions such as the type of the bacterium to be used, and the type of the L-amino acid to be produced.

The carbon source is not particularly limited, so long as the bacterium of the present invention can utilize the chosen carbon source and produce an L-amino acid. Specific examples of the carbon source include, for example, saccharides such as glucose, fructose, sucrose, lactose, galactose, xylose, arabinose, blackstrap molasses, starch hydrolysates, and hydrolysates of biomass, organic acids such as acetic acid, fumaric acid, citric acid, succinic acid, and malic acid, alcohols such as glycerol, crude glycerol and ethanol, and fatty acids. As the carbon source, a single kind of carbon source may be used, or two or more kinds of carbon sources may be used in combination.

The concentration of the carbon source in the medium is not particularly limited, so long as the bacterium of the present invention can proliferate, and an L-amino acid is produced. It is preferable to make the concentration of the carbon source in the medium as high as possible in such a range that the production of L-amino acid is not inhibited. The initial concentration of the carbon source in the medium may be usually in the range of 5 to 30% (W/V), preferably 10 to 20% (W/V). Further, in accordance with the consumption of the carbon source accompanying the progress of the fermentation, the carbon source may be supplementarily added.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid or the like for growth thereof is used, it is preferable to supplement a required nutrient to the medium. For example, in many of L-lysine-producing bacteria, the L-lysine biosynthetic pathway is enhanced and the L-lysine degrading ability is attenuated. Therefore, when such an L-lysine-producing bacterium is cultured, for example, one or more kinds of amino acids selected from L-threonine, L-homoserine, L-isoleucine, and L-methionine are preferably added to the medium.

Further, it is also preferable to add an appropriate amount of a commercially available antifoam to the medium, in order to suppress foaming during the culture.

The culture conditions are not particularly limited so long as the bacterium of the present invention can proliferate, and an L-amino acid is produced. The culture can be performed, for example, under usual conditions used for culturing microorganisms such as bacteria. The culture conditions can be appropriately set according to various conditions such as the type of bacterium to be used, and the type of L-amino acid to be produced.

The culture can be performed by using a liquid medium. For the culture, the bacterium of the present invention cultured on a solid medium such as agar medium may be directly inoculated into a liquid medium, or the bacterium of the present invention cultured in a liquid medium as seed culture may be inoculated into a liquid medium for main culture. That is, the culture may be performed as separate seed culture and main culture. The amount of the bacterium of the present invention contained in the medium at the time of the start of the culture is not particularly limited. For example, seed culture showing OD660 of 4 to 8 can be added to the medium for main culture in an amount of 0.1 to 30 mass %, or 1 to 10 mass %, at the time of the start of the culture.

The culture can be performed as batch culture, fed-batch culture, continuous culture, or a combination of these. Further, when the culture is performed as separate seed culture and main culture, the culture conditions of the seed culture and the main culture may be the same or different. For example, both the seed culture and the main culture may be performed as batch culture. Alternatively, for example, the seed culture may be performed as batch culture, and the main culture may be performed as fed-batch culture or continuous culture.

The culture can be, for example, aerobically performed. For example, the culture can be performed as aeration culture or shaking culture. The oxygen concentration can be controlled to be, for example, 5 to 50%, orabout 10%, of the saturated oxygen concentration. pH of the medium may be, for example, 3 to 10, or 4.0 to 9.5. pH of the medium can be adjusted as required during culture. pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture time may be, for example, 1 hour or longer, 4 hours or longer, 10 hours or longer, or 15 hours or longer, and may be 168 hours or shorter, 120 hours or shorter, 90 hours or shorter, or 72 hours or shorter. Specifically, the culture period may be, for example, 10 to 120 hours. The culture may be continued, for example, until the carbon source contained in the medium is consumed, or until the activity of the bacterium of the present invention is lost. By culturing the bacterium of the present invention under such conditions, an L-amino acid is accumulated in the cells and/or the medium.

Moreover, when L-glutamic acid is produced, the culture can be performed while precipitating L-glutamic acid in the medium by using a liquid medium adjusted to satisfy a condition under which L-glutamic acid precipitates. Examples of the condition under which L-glutamic acid precipitates include, for example, pH of 5.0 to 3.0, pH 4.9 to 3.5, pH 4.9 to 4.0, or about pH 4.7 (European Patent Laid-open No. 1078989). The total period or a partial period of the culture may be performed at the aforementioned pH. The "partial period" may be, for example, 50% or more, 70% or more, 80% or more, 90% or more, 95% or more, or 99% or more, of the total period of the culture.

When a basic amino acid such as L-lysine is produced, there may be employed a method in which the basic amino acid is produced by fermentation using bicarbonate ions and/or carbonate ions as major counter ions for the basic amino acid (Japanese Patent Laid-open (Kokai) No. 2002-65287, U.S. Patent Published Application No. 20020025564, EP 1813677 A). By such a method, a basic amino acid can be produced while reducing the required amount(s) of sulfate ions and/or chloride ions, which have been conventionally used as counter ions for a basic amino acid.

Production of the L-amino acid can be confirmed by known methods used for detection or identification of compounds. Examples of such methods include, for example, HPLC, LC/MS, GC/MS, and NMR. These methods can be used in an appropriate combination.

The produced L-amino acid can be collected by known methods used for separation and purification of compounds. Examples of such methods include, for example, ion-exchange resin method, membrane treatment method, precipitation method, and crystallization method. These methods may be used in an appropriate combination. When the L-amino acid accumulates in cells, the cells can be disrupted with, for example, ultrasonic waves or the like, and then the L-amino acid can be collected by the ion exchange resin method or the like from the supernatant obtained by removing the cells from the cell-disrupted suspension by centrifugation. The L-amino acid to be collected may be a free compound, a salt thereof, or a mixture thereof. Examples of the salt include, for example, sulfate, hydrochloride, carbonate, ammonium salt, sodium salt, and potassium salt.

L-lysine may be, for example, L-lysine in a free form, the hydrochloride salt of L-lysine, the carbonate salt of L-lysine, or a mixture thereof. Further, L-glutamic acid may be, for example, L-glutamic acid in a free form, monosodium L-glutamate (MSG), monoammonium L-glutamate, or a mixture thereof.

Further, when the L-amino acid precipitates in the medium, it can be collected by centrifugation, filtration or the like. L-Amino acid precipitated in the medium and L-amino acid dissolved in the medium may be isolated together after the L-amino acid dissolved in the medium is crystallized.

The collected L-amino acid may contain, for example, bacterial cells, medium components, moisture, and by-product metabolites of the bacterium, in addition to the L-amino acid. Purity of the collected L-amino acid may be, for example, 30% (w/w) or higher, 50% (w/w) or higher, 70% (w/w) or higher, 80% (w/w) or higher, 90% (w/w) or higher, or 95% (w/w) or higher (JP1214636B, U.S. Pat. No. 5,431,933, U.S. Pat. No. 4,956,471, U.S. Pat. No. 4,777,051, U.S. Pat. No. 4,946,654, U.S. Pat. No. 5,840,358, U.S. Pat. No. 6,238,714, US2005/0025878).

An embodiment of the method of the present invention may be a method for producing L-lysine by culturing Escherichia coli having L-lysine-producing ability in a medium to produce and accumulate L-lysine in the medium or cells of the Escherichia coli; and collecting L-lysine from the medium or cells, wherein the expression of a gene of the acpP-fabF operon has been attenuated in the Escherichia coli by modifying an expression control sequence of the gene. An embodiment of the method of the present invention may also be a method for producing L-lysine by culturing Escherichia coli having L-lysine-producing ability in a medium to produce and accumulate L-lysine in the medium or cells of the Escherichia coli; and collecting L-lysine from the medium or cells, wherein the cytosine at the position −34 upstream from the translation initiation site of the acpP gene has been replaced with another base in the Escherichia coli. An embodiment of the method of the present invention may also be a method for producing L-lysine by culturing Escherichia coli having L-lysine-producing ability in a medium to produce and accumulate L-lysine in the medium or cells of the Escherichia coli; and collecting L-lysine from the medium or cells, wherein the cytosine at the position −34 upstream from the translation initiation site of the acpP gene has been replaced with adenine in the Escherichia coli. The aforementioned descriptions concerning the bacterium of the present invention and the method of the present invention can be applied mutatis mutandis to these embodiments.

EXAMPLES

Hereafter, the present invention will be more specifically explained with reference to the following examples.

Example 1

Construction of L-Lysine-Producing Bacterium Showing Reduced Expression of acpP and fabF genes (1)

As the L-lysine-producing bacterium, the E. coli WC196ΔcadAΔldc strain (FERM BP-11027, WO2010/061890, henceforth also referred to as WC196LC strain) was used. A point mutation was introduced in this strain upstream of the acpP-fabF operon, which includes the acpP and fabF genes, by using the method called "Red-driven integration", which was first developed By Datsenko and Wanner (Proc. Natl. Acad. Sci. USA, 2000, vol. 97, No. 12, pp.6640-6645). According to this method, a mutation can be introduced into a strain in one step by using a PCR product obtained by using synthetic oligonucleotides in which a sequence corresponding to a target gene is designed on the 5' end side, and a sequence corresponding to an antibiotic resistance gene is designed on the 3' end side. The procedure is shown below.

PCR was performed by using the chromosomal DNA of the Escherichia coli MG1655 strain (ATCC 47076) as the template, and the synthetic oligonucleotides shown as SEQ ID NOS: 1 and 2 as the primers. The primer of SEQ ID NO: 1 has a sequence corresponding to the sequence around the BglII site of the plasmid pMW118(λattL-Kmr-AattR) (WO2006/093322) at the 5' end of the primer, and a sequence corresponding to a part of upstream sequence of the acpP gene at the 3' end of the primer. The primer of SEQ ID NO: 2 has a sequence corresponding to the sequence around the BglII site of the plasmid pMW118(λattL-Kmr-λattR) (WO2006/093322) at the 5' end of the primer, and a sequence corresponding to a part of downstream sequence of the fabF gene at the 3' end of the primer. The obtained DNA fragment was ligated with the vector pMW118(λattL-Kmr-λattR) that had been treated with the restriction enzyme BglII by using In-Fusion HD Cloning Kit (TAKARA BIO). The E. coli JM109 strain was transformed by using the In-Fusion reaction mixture. A transformant was selected on an L-agar medium containing 50 mg/L of kanamycin. A plasmid was extracted from the transformant, and insertion of the target fragment was confirmed. This plasmid was designated pMW118(λattL-Kmr-λattR)-acpP-fabF.

By using pMW118(λattL-Kmr-λattR)-acpP-fabF as the template, the synthetic oligonucleotides shown as SEQ ID NOS: 3 and 4 as the primers, and QuikChange Site-Directed Mutagenesis Kit (Agilent Technologies), a plasmid introduced with a point mutation was constructed. This mutation replaces the cytosine located 34 bases upstream of the translation initiation site of the acpP gene with adenine. This plasmid was designated pMW118(λattL-Kmr-λattR)-acpP*-fabF.

PCR was performed by using pMW118(λattL-Kmr-λattR)-acpP*-fabF as the template, and the synthetic oligonucleotides shown as SEQ ID NOS: 5 and 6 as the primers. WC196LCacpP* strain was constructed from the E. coli WC196LC strain by using the obtained DNA fragment according to the λ-Red method described in U.S. Patent Published Application No. 2006/0160191 and WO2005/010175. In the WC196LCacpP* strain, cytosine located 34 bases upstream of the translation initiation site of the acpP gene is replaced with adenine. In the λ-red method, a kanamycin resistant recombinant was obtained by performing plate culture on an L-agar medium containing 50 mg/L of kanamycin at 37° C., and selecting a kanamycin resistant recombinant.

The WC196LCacpP* strain was transformed with the plasmid pCABD2 (U.S. Pat. No. 6,040,160), and a transformant was selected on the L-agar medium containing 20 mg/L of streptomycin, to obtain WC196LCacpP*/pCABD2 strain. The plasmid pCABD2 contains a mutant dapA gene derived from Escherichia coli and coding for a dihydrodipicolinate synthase (DDPS) having a mutation for desensitization to feedback inhibition by L-lysine, a mutant lysC gene derived from Escherichia coli and coding for an aspartokinase III having a mutation for desensitization to feedback inhibition by L-lysine, the dapB gene derived from Escherichia coli and coding for dihydrodipicolinate reductase, and the ddh gene derived from Brevibacterium lactofermentum and coding for diaminopimelate dehydrogenase.

Example 2

L-Lysine Production (1)

L-Lysine production was performed by using the prepared WC196LCacpP*/pCABD2 strain. The strain was cultured on the L-medium containing 20 mg/L of streptomycin at 37° C. until OD600 became about 0.6, and a 40% glycerol solution in a volume equal to the volume of the culture medium was added, and the mixture was stirred. Then, the mixture was divided into appropriate volumes, and stored at −80° C. as glycerol stock.

The glycerol stock of the WC196LCacpP*/pCABD2 strain was uniformly applied to the L-agar medium containing 20 mg/L of streptomycin, and cultured at 37° C. for 24 hours. The WC196LC/pCABD2 strain, which is a control strain obtained by introducing pCABD2 into the WC196LC strain, was similarly cultured on the L-agar medium containing 20 mg/L of streptomycin. The grown cells were suspended in 3.0 mL of the L-lysine production medium (MS-Glc medium) shown in Table 1, and the obtained suspension was diluted with the same medium so that OD600 of the suspension became 15. The obtained diluted suspension in a volume of 1.0 mL was inoculated into 19 mL of the L-lysine production medium containing 20 mg/L of streptomycin and contained in a 500 mL-volume Sakaguchi flask, and culture was performed at 37° C. by using a reciprocal shaking culture apparatus. Forty-eight hours after the start of the culture, the amounts of residual glucose and produced L-lysine were quantified.

TABLE 1

L-Lysine production medium (MS-Glc medium)

| | |
|---|---|
| Glucose | 40.0 g/L |
| (NH4)2SO4 | 24 g/L |
| KH2PO4 | 1.0 g/L |
| MgSO4•7H2O | 1.0 g/L |
| FeSO4•7H2O | 0.01 g/L |
| MnSO4•7H2O | 0.008 g/L |
| Yeast Extract | 2.0 g/L |
| CaCO3 (Japanese pharmacopoeia) | 30 g/L |

The medium was adjusted to pH 7.0 with KOH, and autoclaved at 115° C. for 10 minutes, provided that glucose and MgSO4·7H2O were autoclaved separately from the other components. CaCO3 was added after hot air sterilization.

The residual glucose concentrations and L-lysine accumulation concentrations obtained after 48 hours of the culture are shown in Table 2. As compared with the control strain WC196LC/pCABD2, L-lysine yield was greatly improved with the WC196LCacpP*/pCABD2 strain in which the expression of the acpP and fabF genes was reduced.

TABLE 2

Residual glucose concentration and L-lysine accumulation concentration obtained after 48 hours of culture

| | L-Lys accumulation (g/L) | Residual glucose (g/L) |
|---|---|---|
| WC196LC/pCABD2 | 15.0 | 0 |
| WC196LCacpP*/pCABD2 | 20.9 | 0 |

Example 3

Verification of Expression Amount of acpP gene by RT-PCR (1)

The WC196LCacpP*/pCABD2 strain and the WC196LC/pCABD2 strain were each cultured under the same conditions as described in Example 2, and culture broth was sampled after 17 hours of the culture. RNA was extracted from the culture broth by using RNAprotect Bacteria Reagent (Qiagen) and RNeasy Mini Kit (Qiagen). Reverse transcription PCR was performed by using the obtained RNA as the template, and by using PrimeScript RT reagent Kit (Takara Bio). Quantitative PCR was performed by using the obtained cDNA as the template, and the synthetic oligonucleotides shown as SEQ ID NOS: 13 and 14 and the synthetic oligonucleotides shown as SEQ ID NOS: 15 and 16 as the primers, and by using Power SYBR Green PCR Master Mix (Applied Biosystems). The oligonucleotides shown as SEQ ID NOS: 13 and 14 each correspond to the nucleotide sequence of the acpP gene. The oligonucleotides shown as SEQ ID NOS: 15 and 16 each correspond to the internal sequence of ORF of rrsA (16s rRNA). The amount of mRNA of acpP gene was calculated by using rrsA (16s rRNA) as the internal standard.

The amounts of mRNA of acpP gene obtained after 17 hours of the culture were shown in Table 3. The data were shown as the relative value to the amount of mRNA of acpP gene observed in the WC196LC/pCABD2 strain set as 1. As compared with the control strain WC196LC/pCABD2, the amount of mRNA of acpP gene was greatly decreased in the WC196LCacpP*/pCABD2 strain.

TABLE 3

Amount of mRNA of acpP gene obtained after 17 hours of culture

| | |
|---|---|
| WC196LC/pCABD2 | 1 |
| WC196LCacpP*/pCABD2 | 0.52 |

Example 4

Construction of L-Lysine-Producing Bacterium Showing Reduced Expression of acpPand fabF genes (2)

As the L-lysine-producing bacterium, the WC196LC strain is used. The upstream region of the acpPfabFoperon consisting of the acpPand fabFgenes of the strain is replaced with $P_{tac84}$ promoter (Russian Patent Published Application No. 2006/134574) or lac promoter by using the "Red-driven integration" method. The region to be replaced may be a part or the whole of the region of −200 to −1 upstream from the transcription initiation site of the acpP-fabFoperon. For example, the region of −100 to −1, −50 to −1, −30 to −1, or −30 to −10 upstream from the transcription initiation site of the acpP-fabF operon may be replaced.

Hereafter, a strain obtained from the WC196LC strain by replacing the upstream region of the acpP-fabF operon with $P_{tac84}$ promoter is designated WC196LC $P_{tac84acp}$P strain, and a strain obtained from the WC196LC strain by replacing the upstream region of the acpP-fabF operon with lac promoter is designated WC196LC Piac acpP strain.

The WC196LC $P_{tac84acp}$P strain and the WC196LC Piac acpP strain are transformed with the plasmid pCABD2, and transformants are selected on the L-agar medium containing 20 mg/L of streptomycin, to obtain WC196LC $P_{tac84acp}$P/pCABD2 strain and WC196LC Plac acpP/pCABD2 strain.

Example 5

L-Lysine Production Culture (2)

L-Lysine production culture is performed according to the method described in Example 2 by using the WC196LC Ptac84acpP/pCABD2 strain and the WC196LC Plac acpP/pCABD2 strain, which are obtained in Example 4, and the WC196LC /pCABD2 strain as a control strain.

Example 6

Verification of Expression Amount of acpPgene by RT-PCR (2)

The WC196LC Ptac84acpP /pCABD2 strain and the WC196LC Plac acpP/pCABD2 strain, which are obtained in Example 4, and the WC196LC /pCABD2 strain are each cultured under the condition described in Example 2, and the amount of mRNA of acpP gene is calculated by using the method described in Example 3.

Example 7

Construction of L-Threonine-Producing Bacterium Showing Reduced Expression of acpP and fabF genes As the L-threonine-producing bacterium, the *E. coil* TDH-6 strain (Japanese Patent Laid-open (Kokai) No. 2001-346578) is used. The TDH-6 strain can be obtained from the *E. coli* TDH-6/pVIC40 strain (VKPM B-3996) by curing the plasmid pVIC40 (Japanese Patent Laid-open (Kokai) No. 2001-346578). The cytosine located 34 bases upstream of the translation initiation site of the acpP gene of the TDH-6 strain is replaced with adenine by using the method described in Example 1. Alternatively, the upstream region of the acpP-fabF operon of the TDH-6 strain is replaced with $P_{tac84}$ promoter or lac promoter by using the method described in Example 4. The region to be replaced may be a part or the whole of the region of −200 to −1 upstream from the transcription initiation site of the acpPfabFoperon. For example, the region of −100 to −1, −50 to −1, −30 to −1, or −30 to −10 upstream from the transcription initiation site of the acpP-fabF operon may be replaced.

Hereafter, a strain obtained from the TDH-6 strain by replacing cytosine located 34 bases upstream of the translation initiation site of the acpP gene with adenine is designated TDH-6acpP*, a strain obtained from the TDH-6 strain by replacing the upstream region of the acpP-fabF operon with $P_{tac84}$ promoter is designated TDH-6 $P_{tac84acp}$P strain, and a strain obtained from the TDH-6 strain by replacing the upstream region of the acpP-fabF operon with lac promoter is designated TDH-6 $P_{lac}$ acpP strain.

The TDH-6acpP* strain, the TDH-6 $P_{tac84acp}$P strain, and the TDH-6 $P_{lac}$ acpP strain are transformed with the plasmid pVIC40 (U.S. Pat. No. 5,705,371), to obtain TDH-6acpP*/pVIC40 strain, TDH-6 $P_{tac84acp}$P/pVIC40 strain, and TDH-6 $P_{lac}$ acpP/pVIC40 strain, respectively.

Example 8

L-Threonine Production Culture

L-threonine production culture is performed according to the method described in U.S. Pat. No. 7,915,018 by using the TDH-6acpP*/pVIC40 strain, the TDH-6 $P_{tac84acp}$P/pVIC40 strain, and the TDH-6 Piac acpP/pVIC40 strain, which are obtained in Example 7, and the TDH-6/pVIC40 strain as a control strain.

Example 9

Verification of expression amount of acpP gene by RT-PCR (3)

L-threonine production culture is performed according to the method described in U.S. Pat. No. 7,915,018 by using the TDH-6acpP*/pVIC40 strain, the TDH-6 $P_{tac84acp}$P/pVIC40 strain, and the TDH-6 $P_{lac}$ acpP/pVIC40 strain, which are obtained in Example 7, and the TDH-6/pVIC40 strain as a control strain, and the amount of mRNA of acpP gene is calculated by using the culture broth according to the method described in Example 3.

INDUSTRIAL APPLICABILITY

According to the present invention, L-amino acid-producing abilities of bacteria can be improved, and L-amino acids can be efficiently produced.

Explanation of Sequence Listing:
SEQ ID NOS: 1 to 6, Primers
ID NO: 7, Nucleotide sequence of acpP-fabF operon and upstream sequence thereof of *E. coli* MG1655
SEQ ID NO: 8, Amino acid sequence of AcpP protein of *E. coli* MG1655
SEQ ID NO: 9, Amino acid sequence FabF protein of *E. coli* MG1655
SEQ ID NO: 10: Nucleotide sequence of acpP-fabF operon and upstream sequence thereof of Pantoea ananatis AJ13355
SEQ ID NO: 11: Amino acid sequence of AcpP protein of Pantoea ananatis AJ13355
SEQ ID NO: 12: Amino acid sequence of FabF protein of Pantoea ananatis AJ13355
SEQ ID NOS: 13 to 16, Primers

The invention claimed is:

1. A method for producing an L-amino acid comprising:
culturing an *Escherichia coli* bacterium having an L-amino acid-producing ability in a medium so that an L-amino acid is produced and accumulates in the medium or the cells of the *Escherichia coli* bacterium; and
collecting the L-amino acid from the medium or the cells,
wherein the *Escherichia coli* bacterium has been genetically modified to have attenuated but not eliminated expression of the chromosomal acyl carrier protein (acpP) gene as compared to a non-modified *Escherichia coli* bacterium.

2. The method according to claim 1, wherein the expression of the chromosomal acpP gene is attenuated by modifying an expression control sequence of the gene.

3. The method according to claim 1, wherein the expression of the chromosomal beta-ketoacyl-ACP synthase II (fabF) gene is also attenuated but not eliminated in the genetically modified *E. coli*.

4. The method according to claim 1, wherein the expression of the chromosomal acpP gene is attenuated by replacing the cytosine of the chromosomal acpP gene at the nucleotide corresponding to position 177 in the nucleotide sequence of SEQ ID NO: 7 with another base.

5. The method according to claim 4, wherein the base is adenine.

6. The method according to claim 1, wherein the L-amino acid is L-lysine.

7. A method for producing L-lysine comprising:
culturing an *Escherichia coli* bacterium having L-lysine-producing ability in a medium so that L-lysine is produced and accumulates in the medium or the cells of the *Escherichia coli* bacterium; and
collecting the L-lysine from the medium or the cells,
wherein the *Escherichia coli* bacterium has been genetically modified to have attenuated but not eliminated expression of the chromosomal acpP gene as compared with a non-modified *Escherichia coli* bacterium by modifying an expression control sequence of the chromosomal acpP gene.

8. A method for producing L-lysine comprising:
culturing an *Escherichia coli* having L-lysine-producing ability in a medium so that L-lysine is produced and accumulates in the medium or the cells of the *Escherichia coli* bacterium; and
collecting the L-lysine from the medium or the cells,
wherein the *Escherichia coli* bacterium has been genetically modified to have attenuated but not eliminated expression of the chromosomal acpP gene as compared with a non-modified *Escherichia coli* bacterium, wherein the expression of the chromosomal acpP gene is attenuated by replacing the cytosine of the chromosomal acpP gene at the nucleotide corresponding to position 177 of the nucleotide sequence of SEQ ID NO: 7 with another base.

9. A method for producing L-lysine comprising:
culturing an *Escherichia coli* having L-lysine-producing ability in a medium so that L-lysine is produced and accumulates in the medium or the cells of the *Escherichia coli* bacterium; and
collecting the L-lysine from the medium or the cells,
wherein the *Escherichia coli* bacterium has been genetically modified to have attenuated but not eliminated expression of the chromosomal acpP gene as compared with a non-modified *Escherichia coli* bacterium, wherein the expression of the chromosomal acpP gene is attenuated by replacing the cytosine of the chromosomal acpP gene at the nucleotide corresponding to position 177 of the nucleotide sequence of SEQ ID NO: 7 with adenine.

* * * * *